(12) United States Patent
Suzuki et al.

(10) Patent No.: US 12,205,707 B2
(45) Date of Patent: Jan. 21, 2025

(54) METHOD, COMPUTER SYSTEM, AND PROGRAM FOR PREDICTING CHARACTERISTICS OF TARGET COMPOUND

(71) Applicant: Tohoku Institute of Technology, Miyagi (JP)

(72) Inventors: Ikuro Suzuki, Miyagi (JP); Naoki Matsuda, Miyagi (JP)

(73) Assignee: Tohoku Institute of Technology, Miyagi (JP)

( * ) Notice: Subject to any disclaimer, the term of this patent is extended or adjusted under 35 U.S.C. 154(b) by 978 days.

(21) Appl. No.: 17/269,685

(22) PCT Filed: Sep. 27, 2019

(86) PCT No.: PCT/JP2019/038240
§ 371 (c)(1),
(2) Date: Feb. 19, 2021

(87) PCT Pub. No.: WO2020/067463
PCT Pub. Date: Apr. 2, 2020

(65) Prior Publication Data
US 2021/0319853 A1    Oct. 14, 2021

(30) Foreign Application Priority Data
Sep. 28, 2018   (JP) .................. 2018-183378

(51) Int. Cl.
*G16H 30/40*    (2018.01)
*G06F 18/21*    (2023.01)
(Continued)

(52) U.S. Cl.
CPC .......... *G16H 30/40* (2018.01); *G06F 18/214* (2023.01); *G06F 18/2163* (2023.01); *G06N 3/08* (2013.01);
(Continued)

(58) Field of Classification Search
CPC ........ G16H 30/40; G16B 40/00; G16B 45/00; G16C 20/80; G16C 20/70; G06V 20/698;
(Continued)

(56) References Cited

U.S. PATENT DOCUMENTS

2015/0301028 A1* 10/2015 Eggan ................ G01N 33/5023
                                                        435/29
2017/0144970 A1*  5/2017 Rishton .............. A61K 31/4035

FOREIGN PATENT DOCUMENTS

| WO | 03101282 A2 | 12/2003 |
| WO | 2016054503 A1 | 4/2016 |
| WO | 2017223052 A1 | 12/2017 |

OTHER PUBLICATIONS

Jing et al., "Deep learning for drug design: an artificial intelligence paradigm for drug discovery in the big data era", The AAAP Journal (2018) 20:58 DOI: 10.1208/s12248-01800210-0, 2018 (Year: 2018).*
(Continued)

*Primary Examiner* — Tsu-Chang Lee
(74) *Attorney, Agent, or Firm* — Renner, Otto, Boisselle & Sklar, LLP

(57) ABSTRACT

A method for predicting the characteristics of a target compound according to the present invention comprises: (1) a step for receiving activity data on nerve cells for the target compound; (2) a step for converting the activity data into an image; (3) a step for inputting the image into an image recognition model trained by a training data set, the training data set including a plurality of training images obtained by converting the activity data on nerve cells for a plurality of known compounds; and (4) a step for processing the image in the image recognition model and outputting at least one characteristic of the target compound.

20 Claims, 16 Drawing Sheets

(51) Int. Cl.
- *G06F 18/214* (2023.01)
- *G06N 3/08* (2023.01)
- *G06V 20/69* (2022.01)
- *G16B 40/00* (2019.01)
- *G16B 45/00* (2019.01)
- *G16C 20/70* (2019.01)
- *G16C 20/80* (2019.01)

(52) U.S. Cl.
CPC ........... *G06V 20/698* (2022.01); *G16B 40/00* (2019.02); *G16B 45/00* (2019.02); *G16C 20/70* (2019.02); *G16C 20/80* (2019.02); *G06F 2218/10* (2023.01); *G06F 2218/12* (2023.01); *G06V 2201/03* (2022.01)

(58) Field of Classification Search
CPC ............ G06V 2201/03; G06F 18/2163; G06F 18/214; G06F 2218/12; G06F 2218/10; G06N 3/08
USPC .......................................................... 706/20
See application file for complete search history.

(56) References Cited

OTHER PUBLICATIONS

International Search Report for related International Application No. PCT/JP2019/038240 mailed Jan. 7, 2020 and its English translation.
First Office Action for related Japanese Application No. 2018-183378 dated Feb. 15, 2019 and its Machine English Translation.
First Office Action for related Japanese Application No. 2018-183378 dated May 23, 2019 and its Machine English Translation.
Matsuda et al., "Prediction method for convulsion toxicity in humans IPS cell-derived neurons using Artificial intelligence", Annual Meeting of the Japanese Society of Toxicology, Aug. 10, 2018, 45.1(0), P25 and English translation.
Odawara, H. Katoh, N. Matsuda & I. Suzuki, "Physiological maturation and drug responses of human induced pluripotent stem cell-derived cortical neuronal networks in long-term culture", Scientific Reports vol. 6, Article No. 26181 (May 18, 2016).
Extended European Search Report for corresponding European Application No. 19866536.6 dated May 25, 2022.
Yunyi Wu et al.; "Machine Learning Based Toxicity Prediction: From Chemical Structural Description to Transcriptome Analysis", International Journal of Molecular Sciences, vol. 19, No. 8, Aug. 10, 2018, p. 2358. Mar. 26, 2024.
Hongming Chen et al.; "The rise of deep learning in drug discovery", Drug Discovery Today, vol. 23, No. 6, Jan. 31, 2018, pp. 1241-1250.

* cited by examiner

METHOD, COMPUTER SYSTEM, AND PROGRAM FOR PREDICTING CHARACTERISTICS OF TARGET COMPOUND

TECHNICAL FIELD

The present invention relates to a method, a computer system, or a program for predicting a property of a target compound.

BACKGROUND ART

There is data showing that 34% of agents found to be toxic in clinical trials is toxic to the central nervous system.

While researches have been conducted to obtain the activity of a neural network of a human derived neuron or the like with a Micro-Electrode Array (MEA) or the like to study the effect of pharmaceutical products in non-clinical trials (Non Patent Literature 1), an effective evaluation method of toxicity to or efficacy on the central nervous system in nonclinical trials has not been found.

CITATION LIST

Non Patent Literature

[NPL 1] A. Odawara, H. Katoh, N. Matsuda & I. Suzuki, "Physiological maturation and drug responses of human induced pluripotent stem cell-derived cortical neuronal networks in long-term culture", Scientific Reports volume 6, Article number: 26181 (2016)

SUMMARY OF INVENTION

Technical Problem

The objective of the present invention is to provide a method or the like for predicting an unknown property of a target compound in a nonclinical trial.

Solution to Problem

The present invention provides, for example, the following items.

Item 1

A method of predicting at least one property of a target compound, comprising the steps of:
(1) receiving activity data for a neuron in response to the target compound;
(2) converting the activity data into an image;
(3) inputting the image into an image recognition model trained with a training data set, the training data set comprising a plurality of training images from converting activity data for a neuron in response to a plurality of known compounds; and
(4) processing the image in the image recognition model to output at least one property of the target compound.

Item 2

The method of item 1, wherein the activity data for the neuron is obtained using one of a micro-electrode array, $Ca^{2+}$ imaging, and membrane potential imaging.

Item 3

The method of item 1 or 2, wherein the image and the training images are one of a raster plot image of the activity data, a histogram of the activity data, a waveform image of the activity data, a spectrum intensity map from FFT, and a connection map using cross-correlation as an indicator.

Item 4

The method of any one of items 1 to 3, wherein the training data set comprises a divided training image from dividing the training images by a specific time window.

Item 5

The method of item 4, wherein the time window is a constant time.

Item 6

The method of item 4, wherein the time window is set for each of the plurality of training images so that the divided training image comprises a constant number of bursts.

Item 7

The method of item 6, wherein the bursts are detected by converting a plurality of pieces of activity data detected using a micro-electrode array on the neuron into a plurality of raster plot images, arranging the raster plot images in accordance with the number of plots, and detecting a burst in the plurality of arranged raster plot images.

Item 8

The method of any one of items 1 to 7, wherein the image recognition model comprises a property prediction model trained with a training data set and a feature extraction model trained with a training data set, wherein the step (4) comprises:
processing the image in the feature extraction model to extract a feature of the target compound; and
processing the extracted feature in the property prediction model to output at least one property of the target compound.

Item 9

The method of item 8, wherein the training data set for the property prediction model comprises features of the known compounds.

Item 10

The method of item 8 or 9, wherein the training data set for the property prediction model is prepared by steps of:
identifying an optimal learning concentration of the known compounds;
converting activity data for a neuron in response to known compounds at the optimal learning concentration into an image; and
processing the image in the feature extraction model to extract the features of the known compounds.

Item 11

The method of any one of items 8 to 10, wherein the training data set for the property prediction model is from normalizing features obtained from the activity data for the neuron in response to the known compounds with a feature obtained from the activity data for the neuron prior to administering the known compounds.

Item 12

The method of any one of items 8 to 11, wherein the image recognition model further comprises a burst detection model trained with a training data set, wherein the step (4) comprises:

processing the image in the burst detection model to detect a burst;

dividing the image based on the detected burst and processing the divided image in the feature extraction model to extract a feature of the target compound; and processing the extracted feature in the property prediction model to output at least one property of the target compound.

Item 13

The method of item 12, wherein the image inputted into the burst detection model is prepared by steps of:

determining a cycle by analyzing a frequency of activity data for a neuron in response to the target compound; and dividing the image based on the cycle.

Item 14

The method of item 13, wherein the analysis of a frequency of activity data comprises FFT analysis on a histogram obtained from the activity data.

Item 15

The method of any one of items 8 to 14, wherein the training data set for the property prediction model is prepared by steps of:

extracting features of the known compounds with respect to a first neuron sample by processing a plurality of images from converting activity data for the first neuron sample in response to the known compounds in the feature extraction model;

extracting features of the known compounds with respect to a second neuron sample by processing a plurality of images from converting activity data for the second neuron sample in response to the known compounds in the feature extraction model; and comparing the features of the known compounds with respect to the first neuron sample with the features of the known compounds with respect to the second neuron sample to identify a feature that is characteristic to the known compounds.

Item 16

The method of any one of items 8 to 15, wherein the step (4) further comprises:

processing a plurality of images from converting activity data for a plurality of neuron samples in response to the target compound in the feature extraction model to extract a feature of the target compound with respect to each of the plurality of neuron samples; and identifying a feature inputted into the property prediction model from correlation of features of the target compound with respect to each of the plurality of neuron samples.

Item 17

The method of any one of items 1 to 16, wherein the step (4) comprises:

processing the image in the image recognition model to output a plurality of properties comprising a first property and a second property of the target compound;

wherein the second property is associated with the first property.

Item 18

The method of item 17, wherein the image recognition model comprises a plurality of property prediction models trained with a training data set, wherein the step (4) comprises the steps of:

outputting the first property of the target compound using a first property prediction model;

determining, from the plurality of property prediction models, a second property prediction model capable of predicting the second property associated with the first property; and outputting the second property of the target compound using the second property prediction model.

Item 19

A method of constructing an image recognition model for predicting at least one property of a target compound, comprising the steps of:
(1) converting activity data for a neuron in response to a plurality of known compounds into a plurality of training images; and
(2) learning a training data set comprising the plurality of training images.

Item 20

The method of item 19, wherein the activity data for the neuron is obtained using one of a micro-electrode array, $Ca^{2+}$ imaging, and membrane potential imaging.

Item 21

The method of item 19 or 20, wherein the training images are one of a raster plot image of the activity data, a histogram of the activity data, a waveform image of the activity data, a spectrum intensity map from FFT, and a connection map using cross-correlation as an indicator.

Item 22

The method of any one of items 19 to 21, further comprising dividing each of the plurality of training images by a specific time window into a plurality of divided training images.

Item 23

The method of item 22, wherein the time window is a constant time.

Item 24

The method of item 23, wherein the time window is set for each of the plurality of training images so that the images comprise a constant number of bursts in the activity data.

Item 25

The method of item 24, wherein the bursts are detected by converting a plurality of pieces of activity data detected by using a micro-electrode array on the neuron into a plurality of raster plot images, arranging the raster plot images in accordance with the number of plots, and detecting a burst in the plurality of arranged raster plot images.

Item 26

The method of any one of items 19 to 25, wherein the image recognition model comprises a property prediction model for outputting a prediction for at least one property of the target compound and a feature extraction model for extracting a feature of the activity data for the neuron.

Item 27

The method of item 26, wherein the step (2) comprises the steps of:
processing the training images in the feature extraction model to extract features of the known compounds; and
learning a training data set comprising the extracted features to train the property prediction model.

Item 28

The method of item 26 or 27, further comprising the steps of:
identifying an optimal learning concentration of the known compounds; and
converting activity data for a neuron in response to known compounds at the optimal learning concentration into a plurality of training images.

Item 29

The method of any one of items 26 to 28, further comprising a step of training the property prediction model by normalizing features obtained from the activity data for the neuron in response to the known compounds with a feature obtained from the activity data for the neuron prior to administering the known compounds and learning a training data set comprising the normalized features.

Item 30

The method of any one of items 26 to 29, further comprising the steps of:
extracting features of the known compounds with respect to a first neuron by processing a plurality of images from converting activity data for the first neuron in response to the known compounds in the feature extraction model;
extracting features of the known compounds with respect to a second neuron by processing a plurality of images from converting activity data for the second neuron in response to the known compounds in the feature extraction model;
comparing the features of the known compounds with respect to the first neuron with the features of the known compounds with respect to the second neuron to identify a feature that is characteristic to the known compounds; and
learning a training data set comprising the identified feature to train the property prediction model.

Item 31

The method of any one of items 1 to 30, wherein the neuron is a neural stem cell.

Item 32

The method of item 31, wherein the neural stem cell is an iPS cell.

Item 33

The method of any one of items 1 to 32, wherein the at least one property comprises one or more of efficacy, toxicity, and mechanism of action of the compound.

Item 34

A program for predicting at least one property of a target compound, the program being executed in a computer system comprising a processor, the program causing the processor to execute processing comprising:
(1) receiving activity data for a neuron in response to the target compound;
(2) converting the activity data into an image;
(3) inputting the image into an image recognition model trained with a training data set, the training data set comprising a plurality of training images from converting activity data for a neuron in response to a plurality of known compounds; and
(4) processing the image in the image recognition model to output at least one property of the target compound.

Item 35

A computer system for predicting at least one property of a target compound, the computer system comprising:
means for receiving activity data for a neuron in response to the target compound;
means for converting the activity data into an image;
an image recognition model trained with a training data set, the training data set comprising a plurality of training images from converting activity data for a neuron in response to a plurality of known compounds; and
means for outputting at least one property of the target compound.

Item 36

A program for constructing an image recognition model for predicting at least one property of a target compound, the program being executed in a computer system comprising a processor, the program causing the processor to execute processing comprising:
converting activity data for a neuron in response to a plurality of known compounds into a plurality of training images; and
learning the plurality of training images.

Item 37

A computer system for constructing an image recognition model for predicting at least one property of a target compound, the computer system comprising:

means for converting activity data for a neuron in response to a plurality of known compounds into a plurality of training images; and means for learning the plurality of training images.

Advantageous Effects of Invention

The present invention can provide a method or the like of predicting an unknown property (e.g., toxicity to or efficacy on the nervous system) of a target compound in a non-clinical trial.

DESCRIPTION OF EMBODIMENTS

Figure 1:
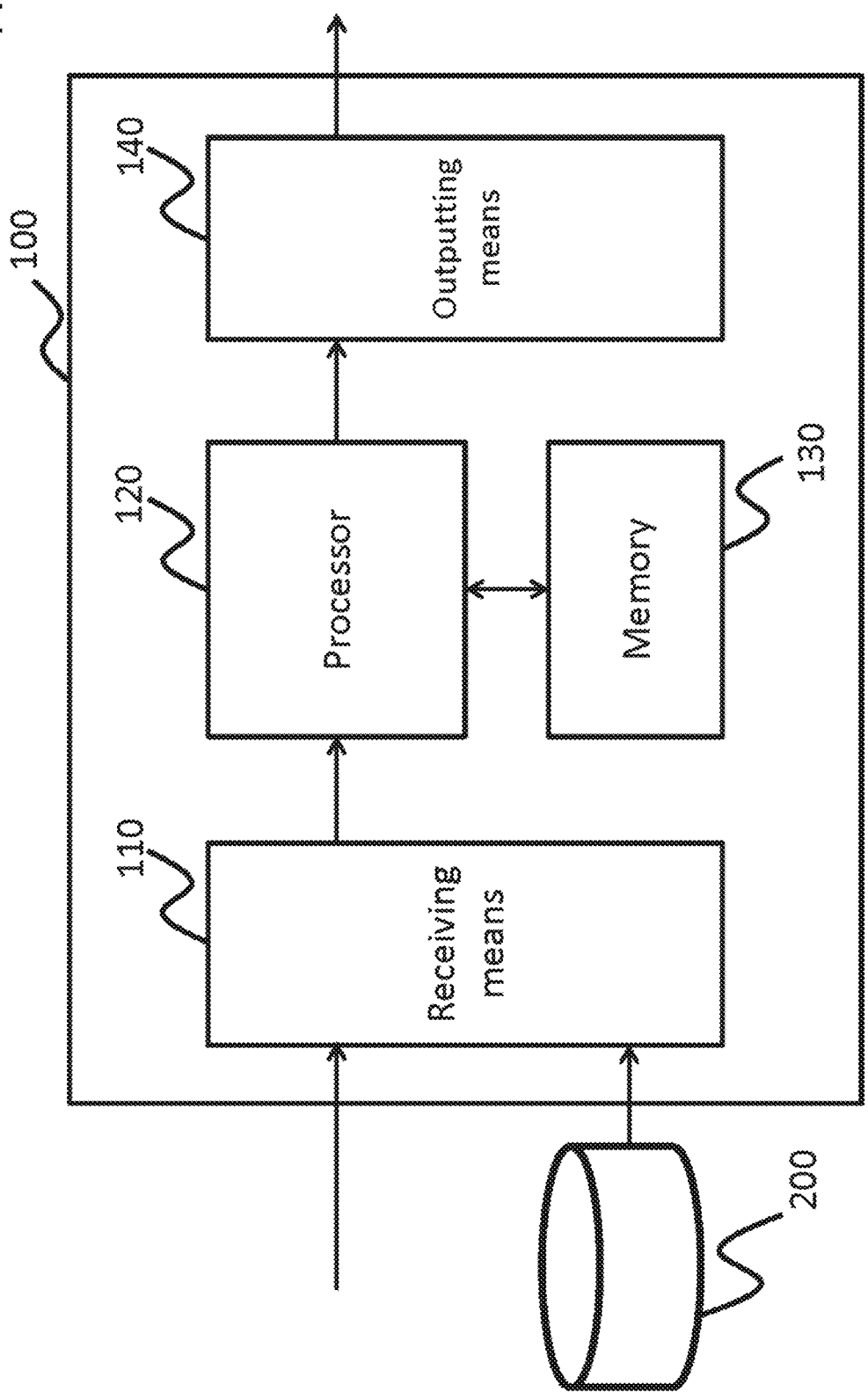
FIG. 1 is a block diagram showing an example of a configuration of a computer system 100 for predicting a property of a target compound of the invention.

The present invention is described hereinafter. The terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definition

As used herein, "target compound" refers to a compound targeted for prediction of a property. A target compound can be an unknown compound or a known compound. Examples of properties of a target compound include, but are not limited to, efficacy, toxicity, and mechanism of action.

As used herein, "efficacy" refers to an effect induced as a result of applying an agent to a subject. If an agent is for example an anti-cancer agent, the efficacy can be a direct effect on a subject such as contraction of a cancerous area under X-ray observation, delay in advancement of cancer, and extended survival of a cancer patient, or an indirect effect such as a reduction in a biomarker correlated with advancement of cancer. As used herein, "efficacy" is intended as an effect under any application condition. If an agent is for example an anti-cancer agent, the efficacy can be an effect in a specific subject (e.g., 80-year-old or older male) or an effect under a specific application condition (e.g., under concomitant use with another anticancer therapy). In one embodiment, an agent can have a single efficacy or a plurality of efficacies. In one embodiment, an agent can have efficacy that varies under different application conditions. In general, efficacy refers to an effect intended to be achieved.

As used herein, "toxicity" refers to an unfavorable effect that is manifested from application of an agent to a subject. In general, toxicity is an effect that is different from the intended effect of an agent. Toxicity can manifest through the same or different mechanism of action from efficacy. If an agent is for example an anti-cancer agent, hepatotoxicity due to killing of normal hepatocytes may manifest concurrently with the efficacy for killing cancer cells via the mechanism of action of suppression of cell proliferation, or toxicity for a neurological dysfunction may manifest via the mechanism of action of membrane stabilization concurrently with efficacy for killing cancer cells via the mechanism of action of suppression of cell proliferation.

As used herein, "mechanism of action" refers to the manner of interaction of an agent with a biological mechanism. If an agent is for example an anti-cancer agent, the mechanism of action can be various levels of events, such as activation of the immune system, killing of cells with a rapid growth rate, blockage of proliferative signaling, blockage of a specific receptor, and inhibition of transcription of a specific gene. If the mechanism of action is identified, efficacy, toxicity, and/or suitable usage form can be predicted based on accumulated information.

As used herein, "about" refers to a range of ±10% from the numerical value that is described subsequent to "about".

1. Prediction of Property of Target Compound

The inventors of the present invention developed an approach of predicting a property of a target compound using artificial intelligence, i.e., AI, in order to evaluate a property of a target compound with respect to the nervous system in non-clinical trials. Such artificial intelligence has learned the relationship between activity data obtained when a plurality of known compounds are administered to a neuron and properties of the known compounds. If activity data obtained when a target compound is administered to a neuron is inputted into such artificial intelligence, the artificial intelligence can predict and output a property of the target compound.

If, for example, activity data obtained when a target compound is administered to a neuron is inputted into such artificial intelligence, the artificial intelligence can predict and output what efficacy the target compound has, what toxicity the target compound has, or what mechanism of action the target compound has. This enables prediction of efficacy, toxicity, or mechanism of action of a target compound in nonclinical trials. For example, this facilitates classification in terms of what known compound the target compound is similar to. Development of safe and sound compounds can also be promoted by predicting the efficacy, toxicity, or mechanism of action of a target compound.

Furthermore, such artificial intelligence can also predict and output, for example, what mechanism of action a target compound has for the predicted efficacy or what mechanism of action a target compound has for the predicted toxicity. In this manner, not only abstract properties, but also specific properties of a target compound can be predicted.

Furthermore, if a known compound is used as a target compound, drug repositioning of the known compound can be performed. Specifically, a new efficacy of the known compound can be found based on the efficacy, toxicity, or mechanism of action predicted by inputting activity data obtained when the known compound is administered to a neuron into such artificial intelligence. This enables discovery of new efficacy of the known compound and drastic reduction in development cost of a therapeutic drug in nonclinical trials.

Such artificial intelligence can be materialized with a computer system for predicting a property of a target compound described below.

The embodiments of the invention are described hereinafter with reference to the drawings.

2. Configuration of a Computer System for Predicting a Property of a Target Compound FIG. 1 shows an example of a configuration of the computer system 100 for predicting a property of a target compound of the invention.

The computer system 100 comprises receiving means 110, a processor 120, a memory 130, and outputting means 140. The computer system 100 can be connected to a database unit 200.

The receiving means 110 is configured to be able to receive data from the outside of the computer system 100. The receiving means 110 can, for example, receive data via a network from the outside of the computer system 100, or receive data from a storage medium (e.g., USB memory, optical disk, or the like) or the database unit 200 connected to the computer system 100. When receiving data via a network, the type of network is not limited. The receiving means 110 can, for example, receive data by utilizing a wireless LAN such as Wi-Fi or receive data via the Internet.

For example, the receiving means 110 receives activity data for a neuron in response to a known compound or target compound. Activity data for a neuron is data that can be obtained by any known methodology.

Activity data for a neuron is, for example, potential data measured using a micro-electrode array (MEA). Such potential data is obtained, for example, by culturing a neuron on an MEA and measuring the activity potential and synaptic current component of the neuron upon administration of a known compound or target compound to the cultured neuron. For example, a CMOS-MEA utilizing CMOS can be used as the MEA. When CMOS-MEA is used, relatively high resolution data can be obtained.

Activity data for a neuron is, for example, potential data measured using a multipoint electrode. Such potential data is obtained, for example, by applying a multipoint electrode on the brain of an animal and measuring the activity potential of a neuron when a known compound or target compound is administered in an animal experiment.

Activity data for a neuron can also be, for example, image data obtained by an optical measurement method. An optical measurement method is, for example, $Ca^{2+}$ imaging. For example, image data is obtained by imaging the activity of a neuron when a known compound or target compound is administered to the neuron through $Ca^{2+}$ imaging. An optical measurement method is, for example, membrane potential imaging using a membrane potential sensitive dye. For example, image data is obtained by imaging the activity of a neuron when a known compound or target compound is administered to the neuron through membrane potential imaging.

In one embodiment, use of MEA can be preferable from the viewpoint of temporal resolution. This is because MEA has higher temporal resolution and is capable of more accurately detecting each spike, so that the amount of information obtained on activity data is greater, compared to $Ca^{2+}$ imaging and membrane potential imaging. Membrane potential imaging has higher temporal resolution than $Ca^{2+}$ imaging.

In another embodiment, use of MEA can be preferable from the viewpoint of long-term measurement. This is because MEA is less invasive compared to $Ca^{2+}$ imaging and membrane potential imaging.

In still another embodiment, use of $Ca^{2+}$ imaging or membrane potential imaging can be preferable from the viewpoint of cell resolution. This is because $Ca^{2+}$ imaging or membrane potential imaging can mark all cells through microscope observation, so that spatial resolution is higher compared to MEA and therefore raster plot images can be readily created in subsequent processing.

In this regard, a neuron is, for example, a neural stem cell. A neural stem cell can be, for example, an animal neural stem cell or a human neural stem cell. A neural stem cell is, for example, an iPS cell. A neuron can be, for example, a primary neuron harvested from an animal.

Data received by the receiving means 110 is passed along to the processor 120 for subsequent processing.

The processor 120 controls the entire operation of the computer system 100. The processor 120 reads out a program stored in the memory 130, and executes the program. This allows the computer system 100 to function as an apparatus for executing a desired step. The processor 120 can be implemented by a single processor or a plurality of processors. Data processed by the processor 120 is passed along to the outputting means 140 for output.

In the memory 130, a program for executing processing in the computer system 100, data required for executing the program, and the like are stored. For example, a program for predicting a property of a target compound (e.g., program for materializing the processing shown in FIG. 9 or 10 described below) or a program for constructing an image recognition model for predicting a property of a target compound (e.g., program for materializing the processing shown in FIG. 5, 6, or 7 described below) is stored in the memory 130. An application implementing any function can be stored in the memory 130. In this regard, how a program is stored in the memory 130 is not limited. For example, a program can be preinstalled in the memory 130. Alternatively, a program can be installed in the memory 130 by being downloaded via a network. The memory 130 can be implemented with any storage means.

The outputting means 140 is configured to be able to output data to the outside of the computer system 100. The mode of how the outputting means 140 is enabled to output information from the computer system 100 is not limited. If the outputting means 140 is, for example, a display screen, information can be outputted on the display screen. Alternatively, if the outputting means 140 is a speaker, information can be outputted via audio from the speaker. Alternatively, if the outputting means 140 is a data writing apparatus, information can be outputted by writing information into a storage medium or the database unit 200 connected to the computer system 100. Alternatively, if the outputting means 140 is a transmitter, data can be outputted by the transmitter sending information out of the computer system 100 via a network. In such a case, the type of network is not limited. For example, a transmitter can transmit information via the Internet or via LAN. For example, the outputting means 140 can output data after converting the data into a format that is compatible with the hardware or software receiving the output, or after adjusting the data to a response rate that is compatible with the hardware or software receiving the output.

For example, activity data for a neuron in response to a known compound can be stored in the database unit 200 connected to the computer system 100. Activity data for a neuron in response to a known compound can be stored while being associated with a property of the known compound. For example, activity data for a neuron in response to a target compound can be stored in the database unit 200. For example, data outputted by the computer system 100 (e.g., predicted property of a target compound) can be stored in the database unit 200. Activity data for a neuron in response to a known compound or target compound stored in the database unit 200 can be stored, for example, after removing data representing an outlier value. This can be accomplished, for example, by utilizing the feature that is characteristic to a compound identified by the processing described below to exclude activity data that does not have the same feature as the feature that is characteristic to the compound as an outlier value. This can refine data that can be stored in the database unit 200.

In the example illustrated in FIG. 1, the database unit 200 is provided external to the computer system 100, but the present invention is not limited thereto. The database unit 200 can also be provided inside the computer system 100. In such a configuration, the database unit 200 can be implemented by the same or different storage means as the storage means implementing the memory 130. In either configuration, the database unit 200 is configured as a storage unit for the computer system 100. The configuration of the database unit 200 is not limited to a specific hardware configuration. For example, the database unit 200 can be comprised of a single hardware part or a plurality of hardware parts. For example, the database unit 200 can be configured as an external hard disk drive of the computer system 100, or as a storage on the cloud connected via a network.

Figure 2:
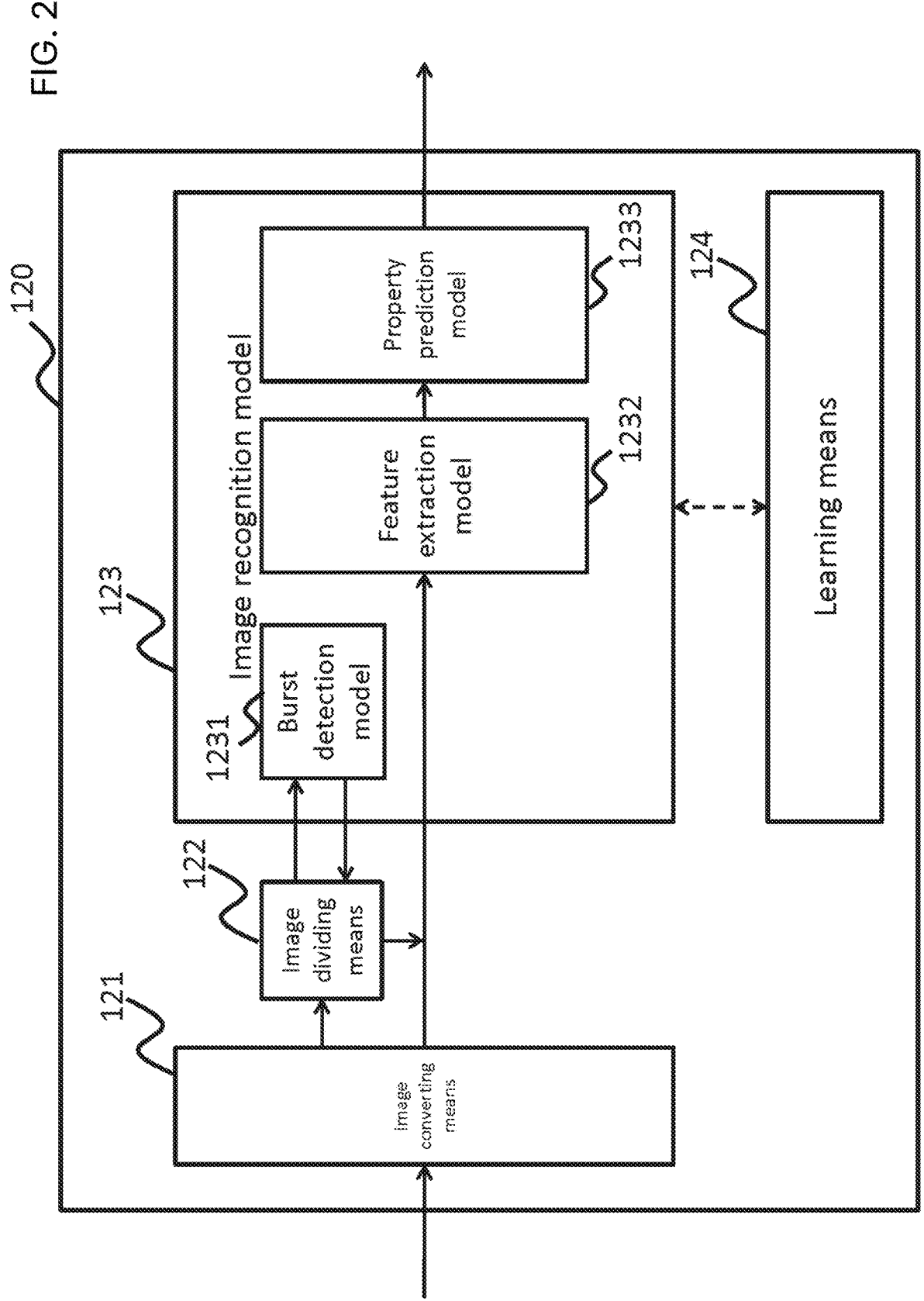
FIG. 2 is a block diagram showing an example of a configuration of a processor 120.

FIG. 2 shows an example of the configuration of the processor 120.

The processor 120 comprises at least image converting means 121 and an image recognition model 123.

The image converting means 121 is configured to convert activity data for a neuron received by the receiving means 110 into image for subsequent processing. Processing for converting activity data into an image is performed using a known conversion methodology.

The image converting means 121 can, for example, convert activity data for a neuron obtained as potential data or activity data for a neuron obtained as image data into a raster plot image. For example, the image converting means 121 can be configured to convert activity data for a neuron obtained as potential data or activity data for a neuron obtained as image data into a histogram. Preferably, the image converting means 121 converts activity data for a neuron obtained as potential data or activity data for a neuron obtained as image data into both a raster plot image and a histogram. This is because this increases the amount of information that is available in subsequent processing to improve the final accuracy of predicting a property of a target compound.

For example, the image converting means 121 can be configured to convert activity data for a neuron obtained as potential data into a waveform image. In such a case, the image converting means 121 can be configured to, for example, generate an image created from arranging waveform images obtained from a plurality of electrodes (e.g., if waveform images are obtained from 64 electrodes, an image arranged in 8×8 or an image arranged in 1×64), or generate an image created from superimposing waveform images obtained from a plurality of electrodes. Use of a waveform image is advantageous in that information on the variation of the size of spikes, information on a low frequency component that is not a spike, or the like, which is not contained in a raster plot image or histogram, can be utilized. However, it should be noted that a waveform image contains noise, so that noise should be eliminated or noise should not be referenced.

For example, the image converting means 121 can be configured to convert activity data for a neuron obtained as potential data into a frequency intensity map by frequency component analysis (e.g., wavelet transform). It can be preferable to perform frequency component analysis at 250 Hz or less. This is because frequency component analysis at 250 Hz or less targets a synaptic current component instead of a spike component for analysis, which enables use of information on a synaptic current component in learning to improve the accuracy of prediction.

Figure 13:
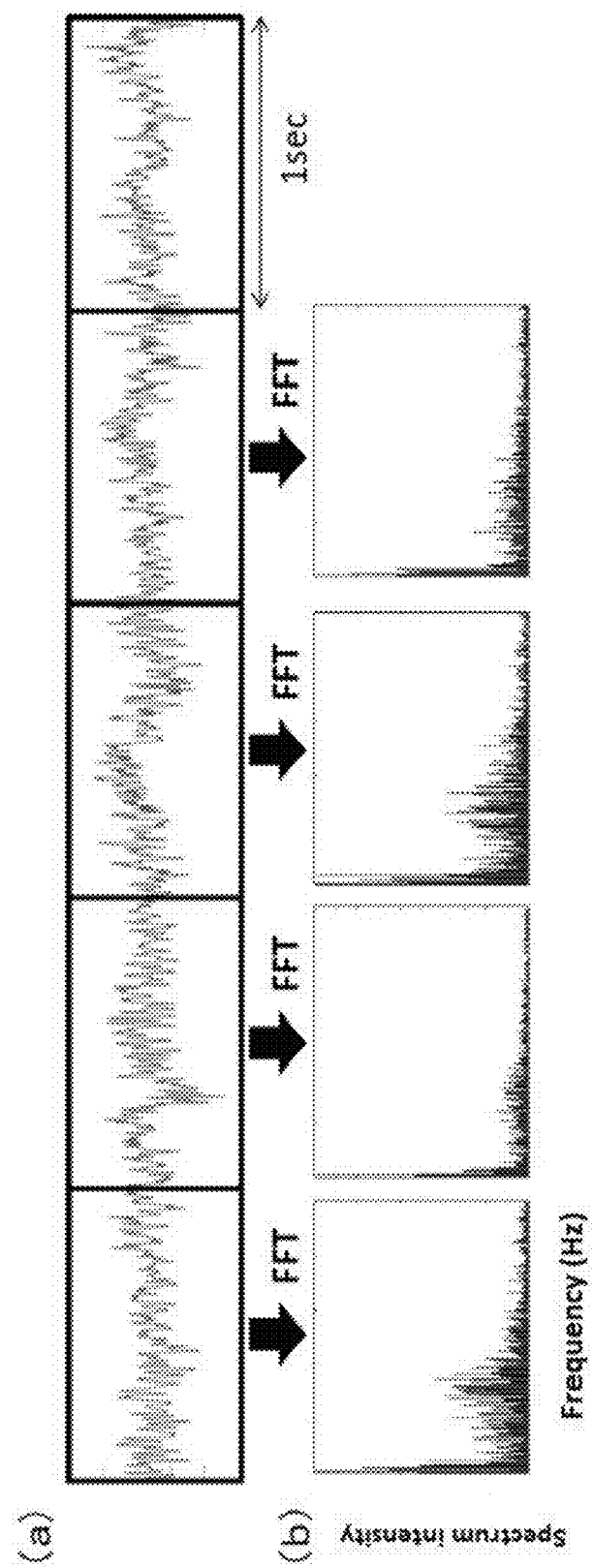
FIG. 13 is a diagram showing an example of obtaining a spectrum intensity map from FFT.

For example, the image converting means 121 can be configured to convert activity data for a neuron obtained as potential data into a waveform (or frequency division waveform) and apply Fourier transform (e.g., fast Fourier transform (FFT)) on a waveform divided by a predetermined time interval (e.g., one second interval) for conversion into a spectrum intensity map. In this regard, a frequency division waveform refers to a waveform from extracting a specific frequency band component. A specific frequency band component can be, for example, a θ wave frequency component (about 4 to about 8 Hz), α wave frequency component (about 8 to about 13 Hz), β wave frequency component (about 13 to about 30 Hz), γ wave frequency component (about 30 to about 100 Hz), or the like. In one embodiment, a frequency band component can be a θ wave frequency component. In another embodiment, a frequency band component can be an α wave frequency component. In still another embodiment, a frequency band component can be a β wave frequency component. In still another embodiment, a frequency band component can be a γ wave frequency component. If, for example, a waveform shown in FIG. 13(*a*) is obtained, the waveform is divided at a one second interval, and FFT is applied to each of the divided waveforms to obtain the spectrum intensity map shown in FIG. 13(*b*). The horizontal axis of a spectrum intensity map is frequency, and the vertical axis is the spectrum intensity. In the example shown in FIG. 13(*b*), spectrum intensities of 1 to 250 Hz are computed. Since a spectrum intensity map represents the distribution of frequency components and not the shape of a waveform (e.g., amplitude, peak position, or the like), use of a spectrum intensity map in learning enables prediction that is not affected by a difference in the shapes of waveforms between samples. A spectrum intensity map also has an advantage of being less susceptible to an effect due to the timing of a time window set for dividing by image dividing means 122 described below. Furthermore, use of a frequency division waveform enables analysis focusing on a phenomenon observed in vivo. For example, a γ wave frequency component of brain waves is enhanced upon an epileptic seizure, so that a property of a target compound associated with epileptic seizure can be analyzed by using a frequency division waveform of a γ wave frequency component.

Figure 14:
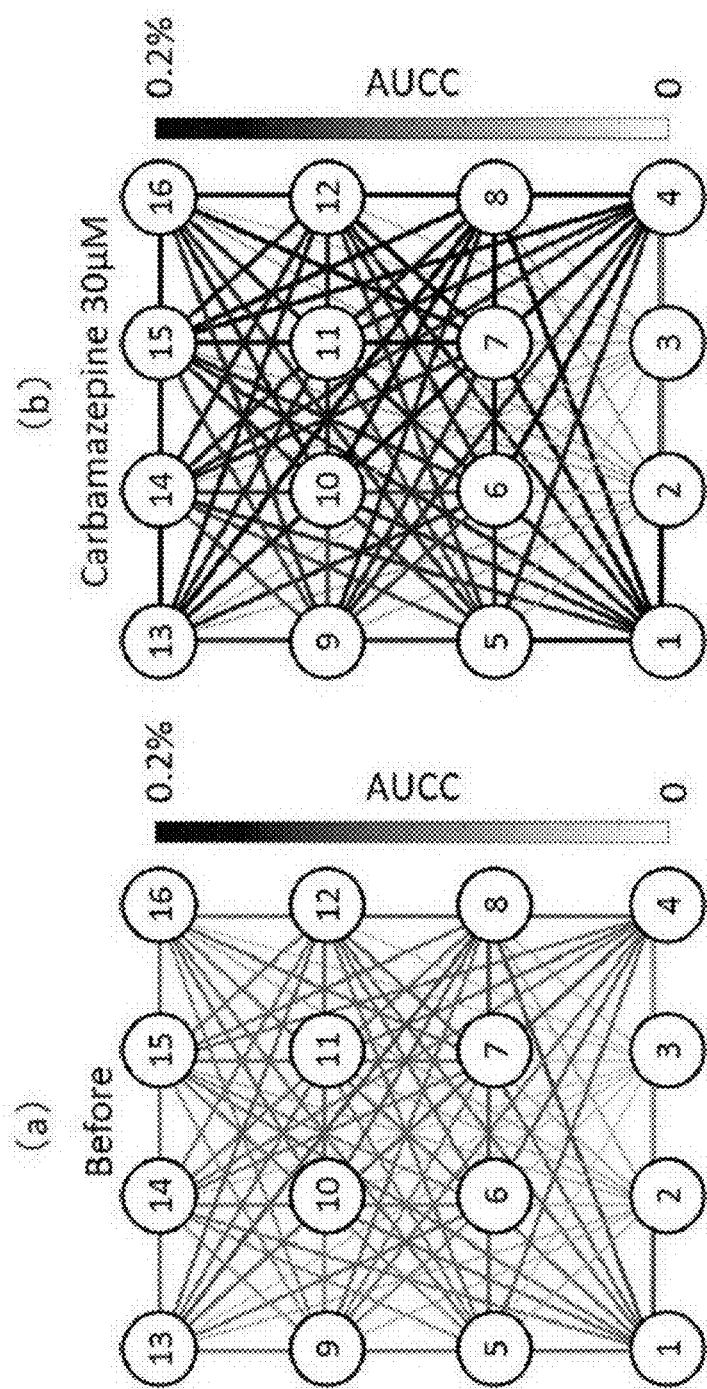
FIG. 14 is a diagram showing an example of a connection map using cross-correlation as an indicator.

For example, the image converting means 121 can be configured to convert activity data for a neuron obtained as potential data into a connection map using cross-correction as an indicator. A connection map can indicate a binding strength between cells by the size of cross-correlation. If, for example, activity data for a neuron obtained by using CMOS-MEA is used, a connection map with a higher resolution can be generated. For example, FIG. 14 shows an example of a connection map using cross-correlation as an indicator. FIG. 14(a) is a connection map showing binding strength between 16 neurons prior to administration of 30 μM of carbamazepine. FIG. 14(b) is a connection map indicating binding strength of 16 neurons after administration of 30 μM of carbamazepine. Each circle with a number assigned represents a cell, and cross-correlation between cells is represented by a line connecting the circles. Cross-correlation is greater for greater AUCC. Since a connection map is data containing spatial information (cell position), use of a connection map in learning enables learning utilizing spatial information, so that the accuracy of prediction is improved. Furthermore, a connection map can represent data from analyzing a pattern of network activity (burst, etc.) with high temporal resolution (e.g., unit of milliseconds), so that the binding strength between neurons at high temporal resolution can be used in learning. Furthermore, learning data can be increased (e.g., 8-fold) by rotating and/or inverting the electrode positions on a connection map.

The image recognition model 123 is configured to output at least one property of a target compound by processing an inputted image. The image recognition model 123 is trained with a training data set. If an image converted from activity data for a neuron in response to a target compound by the image converting means 121 (or an image divided by the image dividing means 122 described below) is inputted into the image recognition model 123, the image recognition model 123 predicts and outputs at least one property of a target compound. A property predicted by the image recognition model 123 is, for example, one or more of efficacy, toxicity, and mechanism of action of the target compound.

It can be preferably for the processor 120 to further comprise the image dividing means 122. This is because the amount of information in data used in subsequently processing can be restricted by comprising the image dividing means 122, so that the processing load can be alleviated. Furthermore, dividing an image and matching the features (e.g., number of bursts) contained in a plurality of images inputted into the image recognition model 123 facilitates processing further and leads to improved prediction accuracy.

The image dividing means 122 is configured to set a time window with a predetermined period and divide an inputted image based on the time window. The predetermined period of a time window can be a fixed value or a variable value. If the predetermined period of a time window is a fixed value, the predetermined period of time window is, for example, a period within a range of about 10 seconds to about 30 seconds, and preferably about 24 seconds. It is preferably that a single divided image contains two or more bursts. With a time window of at least about 10 seconds, a divided image would contain two or more bursts. A greater number of bursts would be contained in a divided image for a longer predetermined time of a time window, but the temporal resolution decreases with a predetermined time of a time window of longer than about 30 seconds. This would decrease the resolution of prediction probability. For example, dividing a 10 minute image by a 20 second time window would result in 30 divided images with a resolution of prediction probability of about 3% (1/30), whereas dividing a 10 minute image by a 30 second time window would result in 20 divided images with a resolution of prediction probability of about 5% (1/20), so that the resolution of prediction probability decreases.

If a predetermined period of a time window is a variable value, the predetermined period of a time window is determined based on the number of bursts contained in an inputted image, so that, for example, the number of bursts contained in the inputted image would be constant. Dividing an image so that the number of bursts contained in a plurality of inputted images would be constant further facilitates processing for training the image recognition model 123 and processing for predicting a property, and improves the prediction accuracy. The number of bursts contained in an inputted image can be, for example, the number of bursts that is determined by a user reading a raster plot image and inputted into the computer system 100. In this regard, identification of bursts is facilitated by rearranging raster plot images in accordance with the number of plots. The number of bursts contained in an inputted image can preferably be a number of bursts determined based on bursts detected by the burst detection model 1231 of the image recognition model 123 described below. This is because use of the burst detection model 1231 reduces intervention of a user, leading to automation of processing.

The processor 120 further comprises learning means 124.

The learning means 124 is configured to train the image recognition model 123 by learning a training data set. A training data set comprises, for example, a plurality of training images from converting activity data for a neuron in response to a plurality of known compounds. It can be preferably for training data set to comprise a divided training image generated by dividing a training image by the image dividing means 122. This is because processing load can be alleviated by restricting the amount of information of a training data set with a divided training image.

A plurality of known compounds used in a training data set has a known property. The learning means 124 learns the relationship between a plurality of training images contained in a training data set and properties of known compounds corresponding to the plurality of training images. For example, the learning means 124 can train the image recognition model 123 by learning a plurality of training images as input supervisor data and corresponding properties as output supervisor data. This enables the image recognition model 123 to predict and output at least one property of a target compound.

Figure 3:
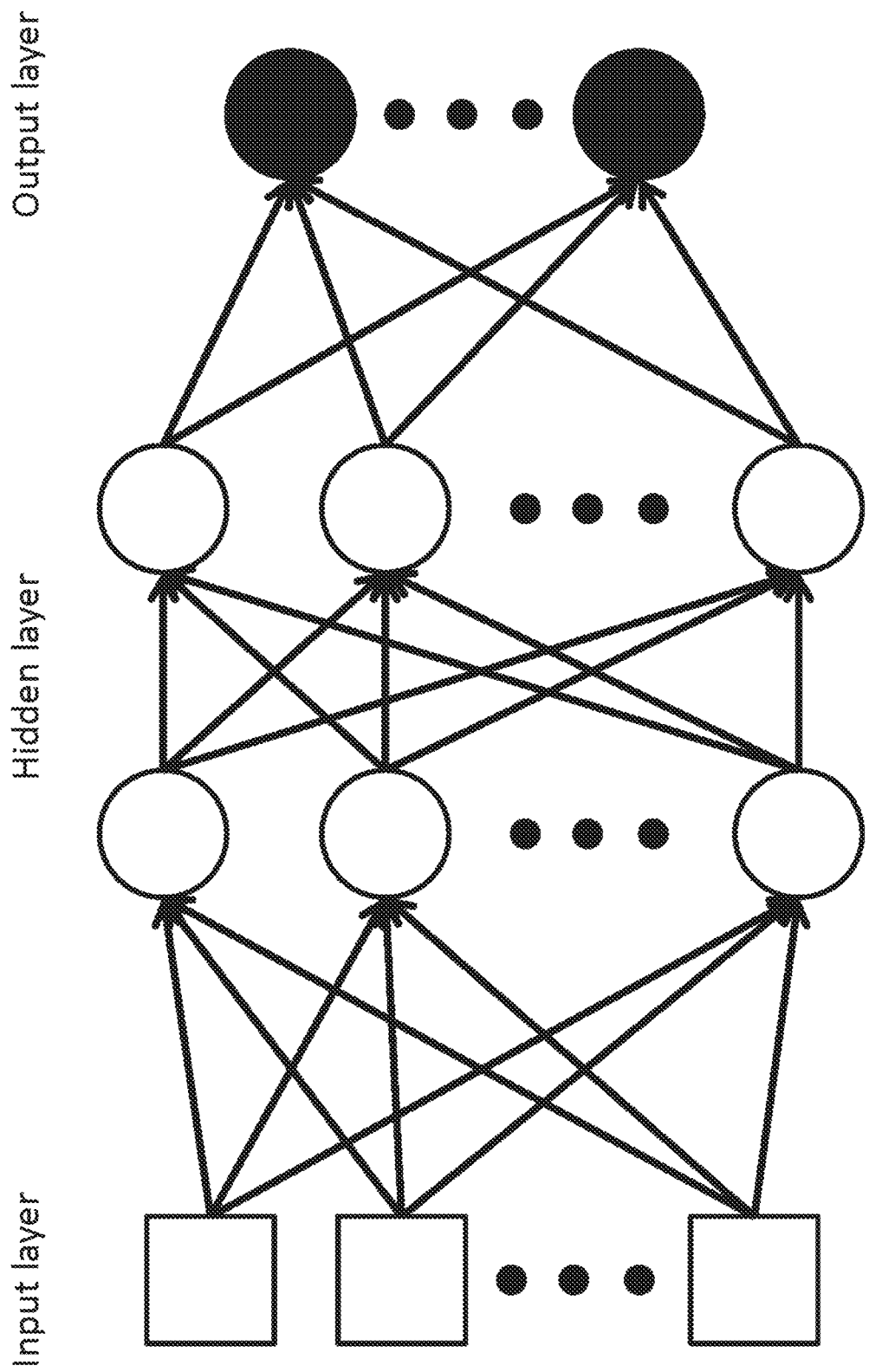
FIG. 3 is a diagram showing an example of a structure of a neural network 300 utilized to construct an image recognition model 123.

FIG. 3 shows an example of a configuration of a neural network 300 utilized to construct the image recognition model 123.

The neural network 300 has an input layer, at least one hidden layer, and an output layer. The number of nodes of an input layer of the neural network 300 corresponds to the number of dimensions of the inputted data. The number of nodes of an output layer of the neural network 300 corresponds to the number of dimensions of the outputted data. A hidden layer of the neural network 300 can comprise any number of nodes. A neural network can be, for example, a convolutional neural network (CNN).

The weighting coefficient of each node of a hidden layer of the neural network 300 can be calculated based on a training data set. Processing for calculating such a weighting coefficient is learning processing. For example, a weight coefficient of each node can be calculated so that a value of an output layer when a plurality of training images from converting activity data for a neuron in response to a plurality of known compounds is inputted in an input layer would be a value indicating a corresponding property of a known compound. This can be performed, for example, by backpropagation. A greater amount of training data sets used in learning can be preferable, but an amout too large can result in overlearning. It can be preferable for a training data set to comprise a divided training image. This is because processing load is alleviated by restricting the amount of information of a training data set with a divided training image. Further, dividing training images and matching the features (e.g., number of bursts) contained in the training images facilitates processing for learning.

When training, for example, for constructing the image recognition model 123 that can predict the presence or absence of toxicity as a property, learning processing utilizes a plurality of training images or divided training images from converting activity data for a neuron in response to a plurality of known compounds whose presence/absence of toxicity is known. When using, for example, known compound A with toxicity, known compound B with toxicity, known compound C with toxicity, known compound D without toxicity, and known compound E without toxicity, sets of (training image inputted into input layer, value of output layer) would be (training image from converting activity data for a neuron in response to known compound A, [1]),
(training image from converting activity data for a neuron in response to known compound B, [1]),
(training image from converting activity data for a neuron in response to known compound C, [1]),
(training image from converting activity data for a neuron in response to known compound D, [0]), and
(training image from converting activity data for a neuron in response to known compound E, [0])
(wherein 1 for an output layer is a value indicating 'with toxicity', and 0 is a value indicating 'without toxicity'). Learning processing calculates a weighting coefficient of each node to satisfy these sets. An ideal output of the neural network 300 with a weighting coefficient of each node calculated in this manner is, for example, a node of an output layer outputting 1 when an image from converting activity data for a neuron in response to known compound A is inputted. However, it is difficult to obtain an ideal output in actuality due to the effect of noise in the activity data for a neuron or the like.

When training, for example, for constructing the image recognition model 123 that can predict efficacy as a property, learning processing utilizes a plurality of training images or divided training images from converting activity data for a neuron in response to a plurality of known compounds whose efficacy is known. When using, for example, known compound A with efficacy of "delay in advancement of cancer", known compound B with efficacy of "contraction of a cancerous area", known compound C with efficacy of "suppression of cancer metastasis", known compound D with efficacy of "delay in advancement of cancer" and "contraction of a cancerous area", and known compound E with efficacy of "contraction of a cancerous area" and "suppression of cancer metastasis", sets of (training image inputted into input layer, value of output layer) would be (training image from converting activity data for a neuron in response to known compound A, [1, 0, 0]), (training image from converting activity data for a neuron in response to known compound B, [0, 1, 0]), (training image from converting activity data for a neuron in response to known compound C, [0, 0, 1]), (training image from converting activity data for a neuron in response to known compound D, [1, 1, 0]), and (training image from converting activity data for a neuron in response to known compound E, [0, 1, 1])

(wherein a value of the first node of an output layer corresponds to the efficacy of "delay in advancement of cancer", a value of the second node corresponds to the efficacy of "contraction of a cancerous area", and a value of the third not corresponds to the efficacy of "suppression of cancer metastasis", 1 is a value indicating 'with efficacy', and 0 is a value indicating 'without efficacy'). Learning processing calculates a weighting coefficient of each node to satisfy these sets. An ideal output of the neural network 300 with a weighting coefficient of each node calculated in this manner is, for example, the first node of an output layer outputting 1 and other nodes outputting 0 when an image from converting activity data for a neuron in response to known compound A is inputted. However, it is difficult to obtain an ideal output in actuality due to the effect of noise in the activity data for a neuron or the like.

Referring back to FIG. 2, it can be preferable for the image recognition model 123 to comprise, for example, a feature extraction model 1232 and at least one property prediction model 1233, as shown in FIG. 2. This is because the accuracy of prediction by the image recognition model 123 is improved thereby.

The feature extraction model 1232 is configured to extract a feature of a target compound by processing an inputted image. The feature extraction model 1232 is trained with a training data set. If an image converted by the image converting means 121 or an image divided by the image dividing means 122 is inputted into the feature extraction model 1232, the feature extraction model 1232 extracts a feature of the image. A feature extracted by a feature extraction model quantifies the characteristic the inputted image has.

For example, the feature extraction model 1232 can utilize an existing image recognition model that has completed learning (e.g., Alex Net, VGG-16, or the like) or can be a model constructed by further training an existing image recognition model that has completed learning, or can be a model constructed by training a neural network shown in FIG. 3. For example, an existing image recognition model that has completed learning, Alex Net, can extract a 4096 dimensional feature from an inputted image. The number of dimensions of a feature that can be extracted by a feature extraction model can be any number that is 2 or greater. While a higher number of dimensions results in improved accuracy of prediction by the image recognition model 123, a higher number of dimensions increases processing load.

If the feature extraction model 1232 is a model constructed by further training an existing image recognition model that has completed learning or a model constructed by training a neural network shown in FIG. 3, the feature extraction model 1232 is trained by the learning means 124. The feature extraction model 1232 is trained so that a feature which captures a characteristic of a point or wave well can be outputted. For example, a weighting coefficient of each node of a hidden layer can be calculated so that a value of an output layer when an image of a point or a wave is inputted into an input layer as a training image is a value indicating a corresponding characteristic of the image of a point or wave.

For example, an image of a point used as a training image is a raster plot image created from various noises (e.g., white noise, brown noise, etc.) or a Braille image, and a value of an output corresponding thereto is various noises (e.g., white noise, brown noise, etc.) and a Braille sentence. For example, an image of a waveform used as a training image is an image of a sine wave, image of various noise waveforms, or an image of a waveform of a different part of the brain, and a value of output corresponding thereto is a corresponding name of the waveform. The feature extraction model 1232 trained in this manner can extract a feature that better captures the characteristic of activity data for a neuron (e.g., raster plot image, waveform image, spectrum intensity map from FFT, and connection map using cross-correlation as an indicator, which are converted from activity data for a neuron) compared to a feature extracted with an existing image recognition model that has completed learning.

The property prediction model 1233 is configured to output at least one property of a target compound by receiving a part or all of the features extracted by the feature extraction model 1232 and processing the received features. The property prediction model 1233 is trained with a training data set. If a feature extracted with the feature extraction model 1232 for an image converted from activity data for a neuron in response to a target compound or an image divided by the image dividing means 122 is inputted into the property prediction model 1233, the property prediction model 1233 predicts and outputs at least one property of the target compound. A property predicted by the property prediction model 1233 is, for example, one or more of efficacy, toxicity, and mechanism of action of a target compound.

The property prediction model 1233 is, for example, a model constructed by training a neural network shown in FIG. 3, and the property prediction model 1233 is trained with the learning means 124. For example, a weighting coefficient of each node can be calculated so that a value of an output layer when a feature extracted by the feature extraction model 1232 from a plurality of training images or divided training images from converting activity data for a neuron in response to a plurality of known compounds is inputted into an input layer would be a value indicating a corresponding property of a known compound.

When training, for example, for constructing the property prediction model 1233 that can predict the presence or absence of toxicity as a property, learning processing utilizes a feature extracted by the feature extraction model 1232 from a plurality of training images or divided training images from converting activity data for a neuron in response to a plurality of known compounds whose presence/absence of toxicity is known. When using, for example, known compound A with toxicity, known compound B with toxicity, known compound C with toxicity, known compound D without toxicity, and known compound E without toxicity, sets of (feature inputted into input layer, value of output layer) would be (feature extracted by the feature extraction model 1232 from a training image from converting activity data for a neuron in response to known compound A, [1]),
(feature extracted by the feature extraction model 1232 from a training image from converting activity data for a neuron in response to known compound B, [1]),
(feature extracted by the feature extraction model 1232 from a training image from converting activity data for a neuron in response to known compound C, [1]),
(feature extracted by the feature extraction model 1232 from a training image from converting activity data for a neuron in response to known compound D, [0]), and
(feature extracted by the feature extraction model 1232 from a training image from converting activity data for a neuron in response to known compound E, [0])
(wherein 1 for an output layer is a value indicating 'with toxicity', and 0 is a value indicating 'without toxicity'). Learning processing calculates a weighting coefficient of each node to satisfy these sets. An ideal output of the neural network 300 with a weighting coefficient of each node calculated in this manner is, for example, a node of an output layer outputting 1 when a feature extracted by the feature extraction model 1232 from an image from converting activity data for a neuron in response to known compound A is inputted. However, it is difficult to obtain an ideal output in actuality due to the effect of noise in the activity data for a neuron or the like.

When training, for example, for constructing the property prediction model 1233 that can predict the mechanism of action as a property, learning processing utilizes a feature extracted by the feature extraction model 1232 from a plurality of training images or divided training images from converting activity data for a neuron in response to a plurality of known compounds whose mechanism of action is known. When using, for example, known compound A with a mechanism of action of "activation of the immune system", known compound B with a mechanism of action of "killing of cells with a rapid growth rate", known compound C with a mechanism of action of "blockage of proliferative signaling", known compound D with a mechanism of action of "blockage of a receptor", and known compound E with a mechanism of action of "inhibition of transcription of a gene", sets of (feature inputted into input layer, value of output layer) would be (feature extracted by the feature extraction model 1232 from a training image from converting activity data for a neuron in response to known compound A, [1, 0, 0, 0, 0]),
(feature extracted by the feature extraction model 1232 from a training image from converting activity data for a neuron in response to known compound B, [0, 1, 0, 0, 0]),
(feature extracted by the feature extraction model 1232 from a training image from converting activity data for a neuron in response to known compound C, [0, 0, 1, 0, 0]),
(feature extracted by the feature extraction model 1232 from a training image from converting activity data for a neuron in response to known compound D, [0, 0, 0, 1, 0]), and
(feature extracted by the feature extraction model 1232 from a training image from converting activity data for a neuron in response to known compound E, [0, 0, 0, 0, 1]),
(wherein a value of the first node of an output layer corresponds to the mechanism of action of "activation of the immune system", a value of the second node corresponds to the mechanism of action of "killing of cells with a rapid growth rate", a value of the third node corresponds to the mechanism of action of "blockage of proliferative signaling", a value of the fourth node corresponds to the mechanism of action of "blockage of a receptor", a value of the fifth node corresponds to the mechanism of action of "inhibition of transcription of a gene", 1 is a value indicating 'with the mechanism of action', and 0 is a value indicating 'without the mechanism of action'). Learning processing calculates a weighting coefficient of each node to satisfy these sets. An ideal output of the neural network 300 with a weighting coefficient of each node calculated in this manner is, for example, the first node of an output layer outputting 1 and other nodes outputting 0 when a feature extracted by the feature extraction model 1232 from an image from converting activity data for a neuron in response to known compound A is inputted. However, it is difficult to obtain an ideal output in actuality due to the effect of noise in the activity data for a neuron or the like.

The image recognition model 123 can comprise a plurality of the property prediction models 1233. If the image recognition model 123 comprises a plurality of property prediction models 1233, each of the plurality of property prediction models 1233 can be trained, for example, by the same processing as the learning processing described above. For example, the property prediction model 1233 can be selectively utilized in accordance with a property to be predicted by varying a property predicted by each of the plurality of property prediction models 1233. This can alleviate processing load in leaning of each of the plurality of property prediction models 1233 and improve the accuracy when predicting various properties.

It can be preferable for the image recognition model 123 to further comprise the burst detection model 1231. This is because the accuracy of prediction by the image recognition model 123 is further improved thereby.

The burst detection model 1231 is configured to detect a burst contained in activity data for a neuron by processing an inputted image. The burst detection model 1231 is trained with a training data set. When an image or a divided training image converted from activity data for a neuron in response to a target compound by the image converting means 121 is inputted into the burst detection model 1231, the burst detection model 1231 detects a burst contained in the activity data for a neuron.

The burst detection model 1231 is, for example, a model constructed by training a neural network shown in FIG. 3, and the burst detection model 1231 is trained with the learning means 124. For example, a weighting coefficient of each node can be calculated so that a value of an output layer when a plurality of training images or divided training images from converting activity data for a neuron in response to a plurality of known compounds is inputted into an input layer would be a value indicating a burst region in the image.

Figure 4A:
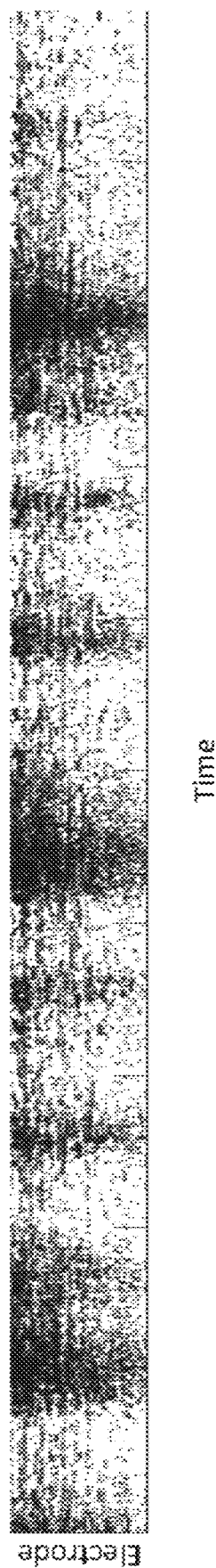
FIG. 4A is a diagram showing an example of a raster plot image used for training a burst detection model 1231.
Figure 4B:
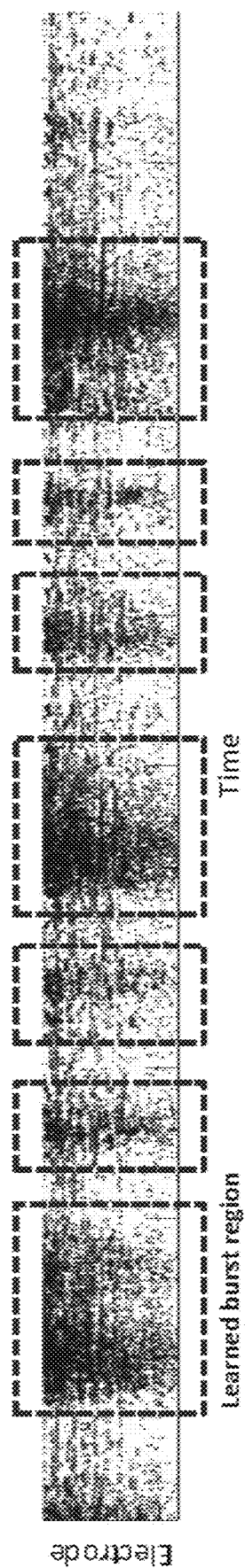
FIG. 4B is a diagram showing an example of a raster plot image used for training the burst detection model 1231.

For example, the burst detection model 1231 is trained using the raster plot images shown in FIGS. 4A and 4B. The raster plot images shown in FIGS. 4A and 4B are images from rearranging electrodes in the order of greater number of firing. The raster plot image shown in FIG. 4A is inputted into an input layer as a training image, and a weighting coefficient of each node can be calculated so that data with a labeled learned burst region as shown in FIG. 4B would be a value of an output layer. The labeled data can be, for example, data indicating a start time and end time of a burst. A weighting coefficient of each node is calculated by using a plurality of sets of such training images. In this regard, it can be preferable for an inputted raster plot image to be a raster plot image divided by the image dividing means 122. This is because processing load is alleviated by restricting the amount of information in an inputted raster plot image. Further, the features (e.g., number of bursts) contained in inputted raster plot images can be matched to further facilitate processing.

Figure 4C:
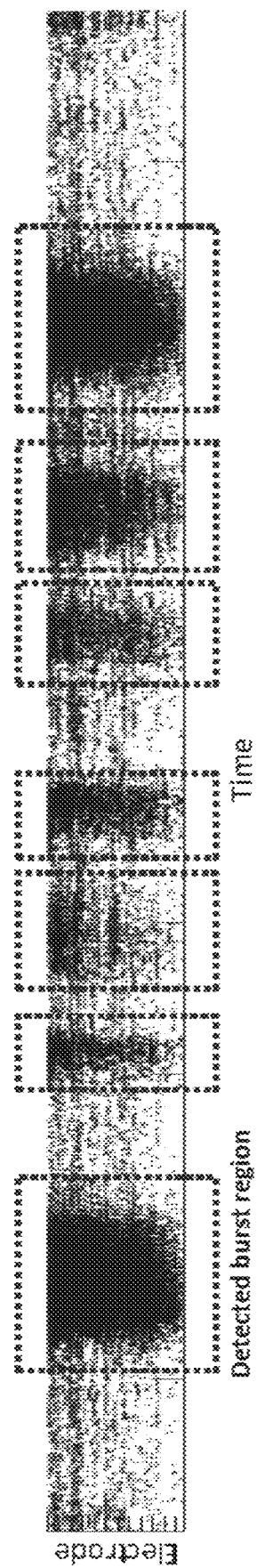
FIG. 4C is a diagram showing an example of a burst region detected by the burst detection model 1231.

If a raster plot image or a divided raster plot image converted from activity data for a neuron in response to a target compound by the image converting means 121 is inputted into the burst detection model 1231 trained in this manner, the burst detection model 1231 can output, for example, the start time and end time of a burst. A burst region within a raster plot image can be detected thereby as shown in FIG. 4C.

For example, the burst detection model 1231 can be trained using a histogram instead of the raster plot images shown in FIGS. 4A and 4B. Specifically, a weighting coefficient of each node can be calculated so that data with a labeled burst region of a histogram would be a value of an output layer after inputting a histogram into an input layer as a training image. In this regard, it can be preferable for an inputted histogram to be a histogram divided by the image dividing means 122. This is because processing load can be alleviated by restricting the amount of information in an inputted histogram. Further, the features (e.g., number of bursts) contained in inputted histograms can be matched to further facilitate processing.

If a histogram or a divided histogram converted from activity data for a neuron in response to a target compound by the image converting means 121 is inputted into the burst detection model 1231 trained in this manner, the burst detection model 1231 can output, for example, the start time and end time of a burst. A burst region within a histogram can be detected thereby. However, a histogram does not have pattern information that a raster plot image has, such that there is less information compared to a raster plot image. Thus, the burst detection model 1231 trained using a raster plot image generally has better accuracy than the burst detection model 1231 trained using a histogram.

The accuracy of the burst detection model 1231 can be improved by training the burst detection model 1231 using a combination of at least two of a raster plot image, a histogram, and a waveform image. Preferably, the accuracy of the burst detection model 1231 can be improved by training the burst detection model 1231 using both a raster plot image and a histogram.

For example, a power spectrum is deduced by frequency analysis (e.g., FFT or the like) on a histogram converted from activity data for a neuron in response to a known compound by the image converting means 121. The maximum peak frequency is then determined from the power spectrum, and a cycle is determined from the maximum peak frequency. A raster plot image converted from activity data for a neuron in response to a known compound is then divided based on the cycle to generate a divided raster plot image. A weighting coefficient of each node can be calculated so that data with a labeled learned burst region would be a value of an output layer after inputting the divided raster plot image into an input layer as a training image.

If a raster plot image or a divided raster plot image converted from activity data for a neuron in response to a target compound by the image converting means 121 is inputted into the burst detection model 1231 trained in this manner, the burst detection model 1231 can output, for example, the start time and end time of a burst, and a burst region within a raster plot image can be detected thereby. In this regard, a divided raster plot image that is inputted can be an image divided based on a histogram described above. Use of both a raster plot image and a histogram enables detection of a burst region with better accuracy than use of a raster plot image or a histogram alone.

A burst detected by the burst detection model 1231 is used by the image dividing means 122 to divide an image inputted into the feature extraction model 1232.

In the example shown in FIG. 1, each constituent element of the computer system 100 is provided within the computer system 100, but the present invention is not limited thereto. Any of the constituent elements of the computer system 100 can also be provided external to the computer system 100. If, for example, each of the processor 120 and memory 130 is comprised of separate hardware parts, each hardware part can be connected via any network. The type of such a network is not limited. Each hardware part can be connected, for example, via LAN, wirelessly, or with a wire. The computer system 100 is not limited to a specific hardware configuration. For example, the processor 120 comprised of an analog circuit instead of a digital circuit is also within the scope of the invention. The configuration of the computer system 100 is not limited to those described above, as long as the function thereof can be materialized.

In the example shown in FIG. 2, each constituent element of the processor 120 is provided within the same processor 120, but the present invention is not limited thereto. A configuration with each constituent element of the processor 120 dispersed in a plurality of processor units is also within the scope of the invention.

Figure 5:
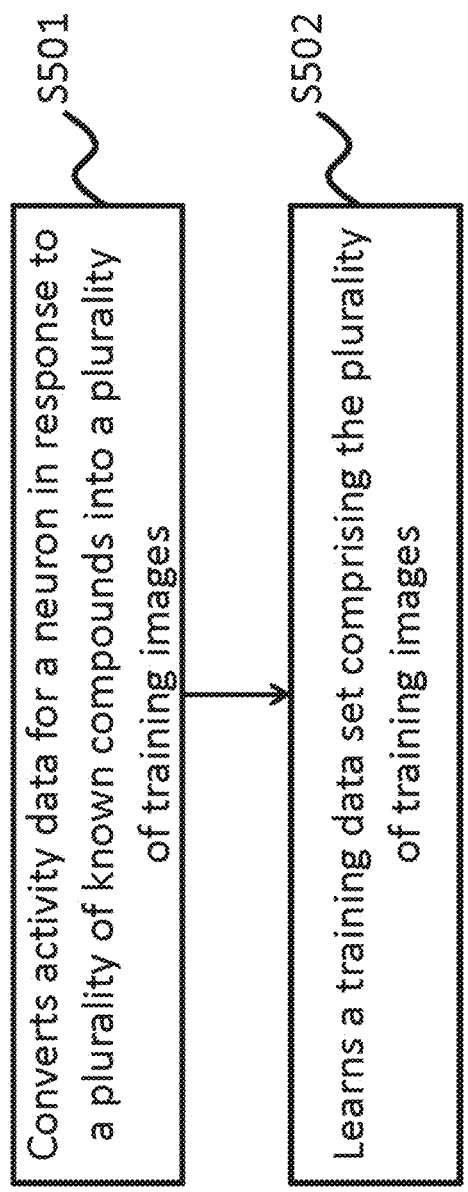
FIG. 5 is a flowchart showing an example of processing in the computer system 100 for predicting a property of a target compound.

3. Processing in a Computer System for Predicting a Property of a Target Compound FIG. 5 shows an example of processing in the computer system 100 for predicting a property of a target compound. The example shown in FIG. 5 describes processing 500 for constructing the image recognition model 123 for predicting a property of a target compound.

When the computer system 100 receives activity data for a neuron in response to a plurality of known compounds via the receiving means 110, the received activity data is passed along to the processor 120.

At step S501, the processor 120 converts the activity data for the neuron in response to a plurality of known compounds into a plurality of training images. For example, the image converting means 121 of the processor 120 converts the activity data for the neuron in response to a plurality of known compounds into at least one of a raster plot image, histogram, waveform image, spectrum intensity map from FFT, and connection map using cross-correlation as an indicator. In this regard, each of the plurality of known compounds is assumed to have at least one known property.

At step S502, the processor 120 learns a training data set comprising a plurality of training images. For example, the learning means 124 of the processor 120 learns the relationship between the plurality of training images and properties of known compounds corresponding to the plurality of training images. This is performed, for example, by calculating a weighting coefficient of each node so that a value of an output layer when a plurality of training images are inputted into an input layer would be a value indicating a corresponding property of a known compound, as described above in reference to FIG. 3.

Figure 6:
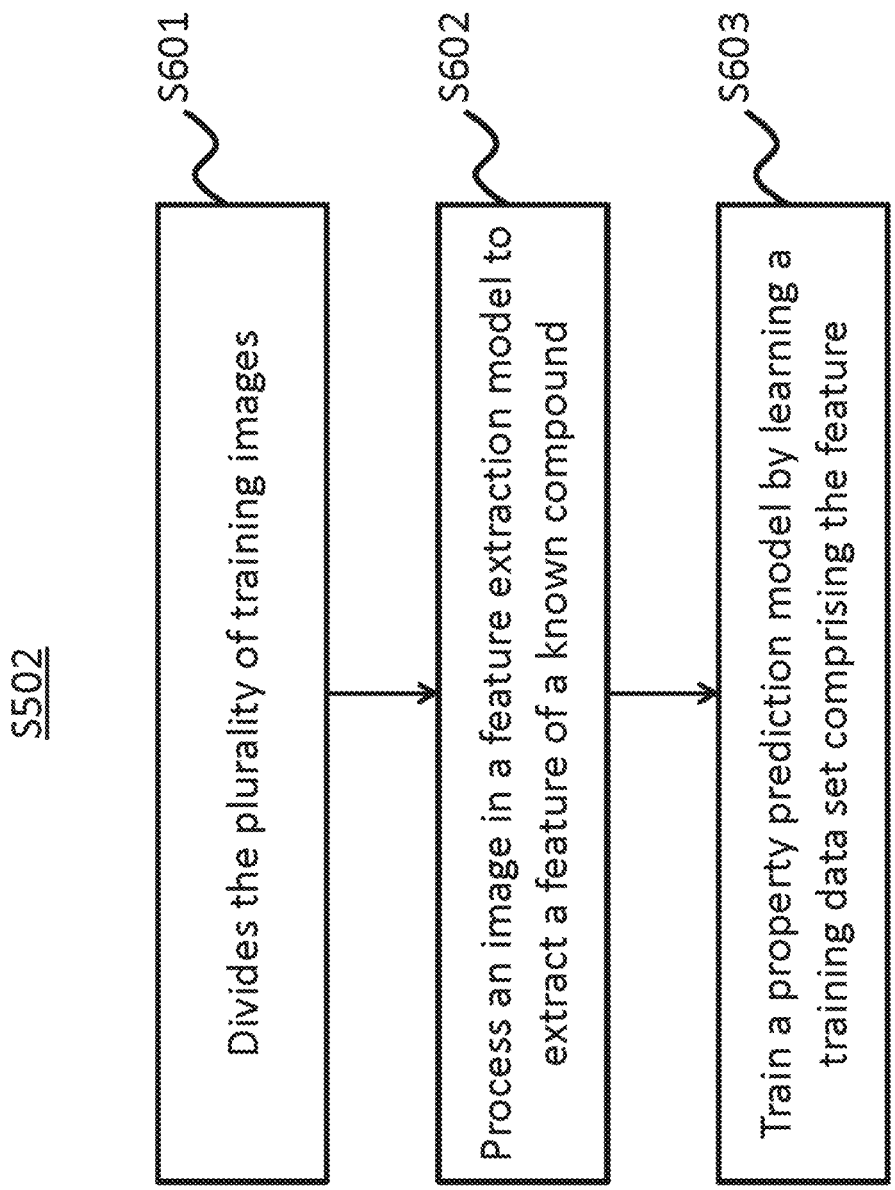
FIG. 6 is a flowchart showing an example of processing of learning by the processor 120 at step S502.

FIG. 6 shows an example of processing of learning by the processor 120 at step S502.

At step S601, the image dividing means 122 of the processor 120 divides a plurality of training images. For example, the image dividing means 122 divides a plurality of training images based on a time window of a predetermined period with a fixed value or variable value. It can be preferable to set a predetermined period for each of the plurality of training images so that each of the plurality of divided training images after the division comprises a constant number of bursts. This is because this can make the number of bursts contained in a plurality of divided training images to be consistent and reduce the difference between samples that is present in activity data for a neuron. For example, a difference between samples can be present not only between samples supplied from different vendors, but also between samples supplied from the same vendor. For example, a difference can be present between samples within the same lot of samples supplied from the same vendor, and a difference can be present between lots, and a difference can be present between supply dates. A difference can also be present between facilities where a test is performed, and between people conducting a test. A reduction in these differences would improve the accuracy of learning and improve the final accuracy of the image recognition model 123.

For example, a plurality of training images can be divided based on the number of bursts using the burst detection model 1231. It is assumed that the burst detection model 1231 has been already trained using training data so that a burst region can be identified. If, for example, a plurality of training images are inputted into the burst detection model 1231, the burst detection model 1231 identifies a burst region of each of the plurality of training images. A predetermined period of a time window is then determined for each of the plurality of training images so that each image contains a constant number of bursts based on the identified burst regions. Each of the plurality of training images is divided by the time window with the predetermined period that has been determined.

When the plurality of training images are divided, at step S602, the divided training images are inputted into the feature extraction model 1232, and the feature extraction model 1232 processes the divided training images to extract a feature of a known compound. It is assumed that the feature extraction model 1232 has been already trained with a training data set as described above. The feature extraction model 1232 extracts a multidimensional feature of the divided training images. For example, an existing image recognition model that has completed learning, Alex Net, extracts a 4096 dimensional feature from a divided training image.

Once a feature is extracted, at step S603, the learning means 124 of the processor 120 trains the property prediction model 1233 by learning a training data set comprising the feature. The learning means 124 learns, for example, the relationship between a multidimensional feature and a corresponding property of a known compound. For example, this can involve calculation of a weighting coefficient of each node so that a value of an output layer when a feature is inputted into an input layer would be a value indicating a corresponding property of a known compound as described above.

At step S603, a feature used in learning can be configured to be restricted to a feature that is characteristic to a known compound. If, for example, a 100 dimensional feature is a feature that is characteristic to a known compound among 4096 dimensional features extracted at step S602, only the 100 dimensional feature can be used in learning.

An example of training to construct the property prediction model 1233 using a feature restricted to a feature that is characteristic to a known compound is described. This is described by assuming, for simplicity, that a 10 dimensional feature is extracted at step S602. For example, it is assumed that features that are characteristic to known compound A are identified as features of the first to third dimensions, features that are characteristic to known compound B are identified as features of the second and seventh dimensions, and features that are characteristic to known compound C are identified as features of the third and sixth to seventh dimensions. In this regard, features used in learning are features of the first to third and sixth to seventh dimensions for a total of 5 dimensions among 10 dimensions of features. This can reduced the number of nodes of an input layer of the property prediction model 1233 from 10 to 5. Features inputted into an input layer would be known compound A=[1, 1, 1, 0, 0]
known compound B=[0, 1, 0, 0, 1]
known compound C=[0, 0, 1, 1, 1]

(wherein the value of the first node of the input layer corresponds to the feature of the first dimension, the value of the second node of the input layer corresponds to the feature of the second dimension, the value of the third node of the input layer corresponds to the feature of the third dimension, the value of the fourth node of the input layer corresponds to the feature of the sixth dimension, and the value of the fifth node of the input layer corresponds to the feature of the seventh dimension).

This can reduce the amount of information used in learning and can lead to improved efficiency of learning, alleviation of processing load, and prevention of overlearning.

Figure 7:
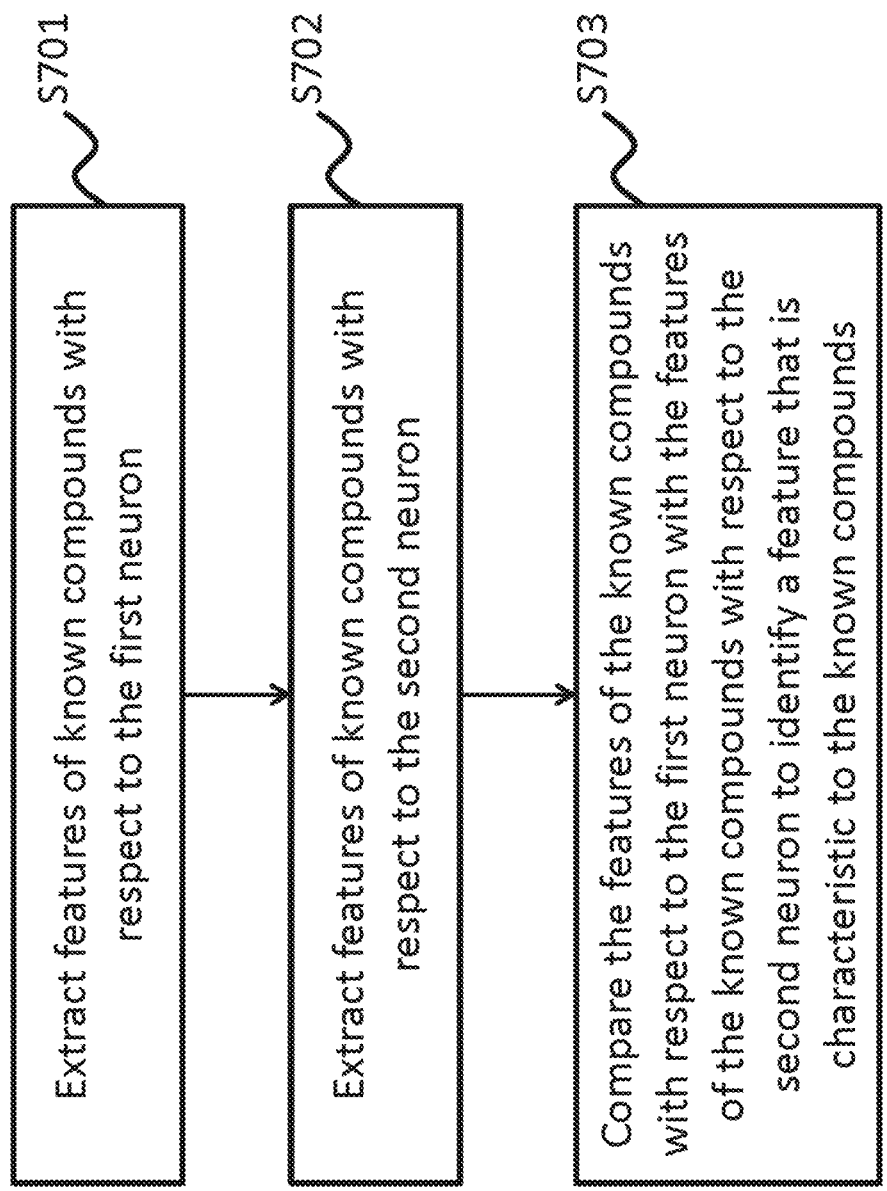
FIG. 7 is a flowchart showing an example of processing for identifying a feature that is characteristic to a known compound.

A feature that is characteristic to a known compound is identified, for example, by the processing shown in FIG. 7.

FIG. 7 shows an example of processing for identifying a feature that is characteristic to a known compound.

At step S701, a feature of a known compound with respect to a first neuron is extracted. A feature of a known compound with respect to a first neuron can be extracted, for example, from an image (or divided image) converted from activity data for the first neuron in response to a known compound by using the feature extraction model 1232.

At step S702, a feature of a known compound with respect to a second neuron is extracted. The second neuron is a neuron that is different from the first neuron. A feature of a known compound with respect to a second neuron can be extracted, for example, from an image (or divided image) converted from activity data for the second neuron in response to a known compound by using the feature extraction model 1232.

At step S703, the feature of the known compound with respect to the first neuron extracted at step S701 is compared to the feature of the known compound with respect to the second neuron extracted at step S702 to identify a feature that is characteristic to the known compound.

Figure 8:
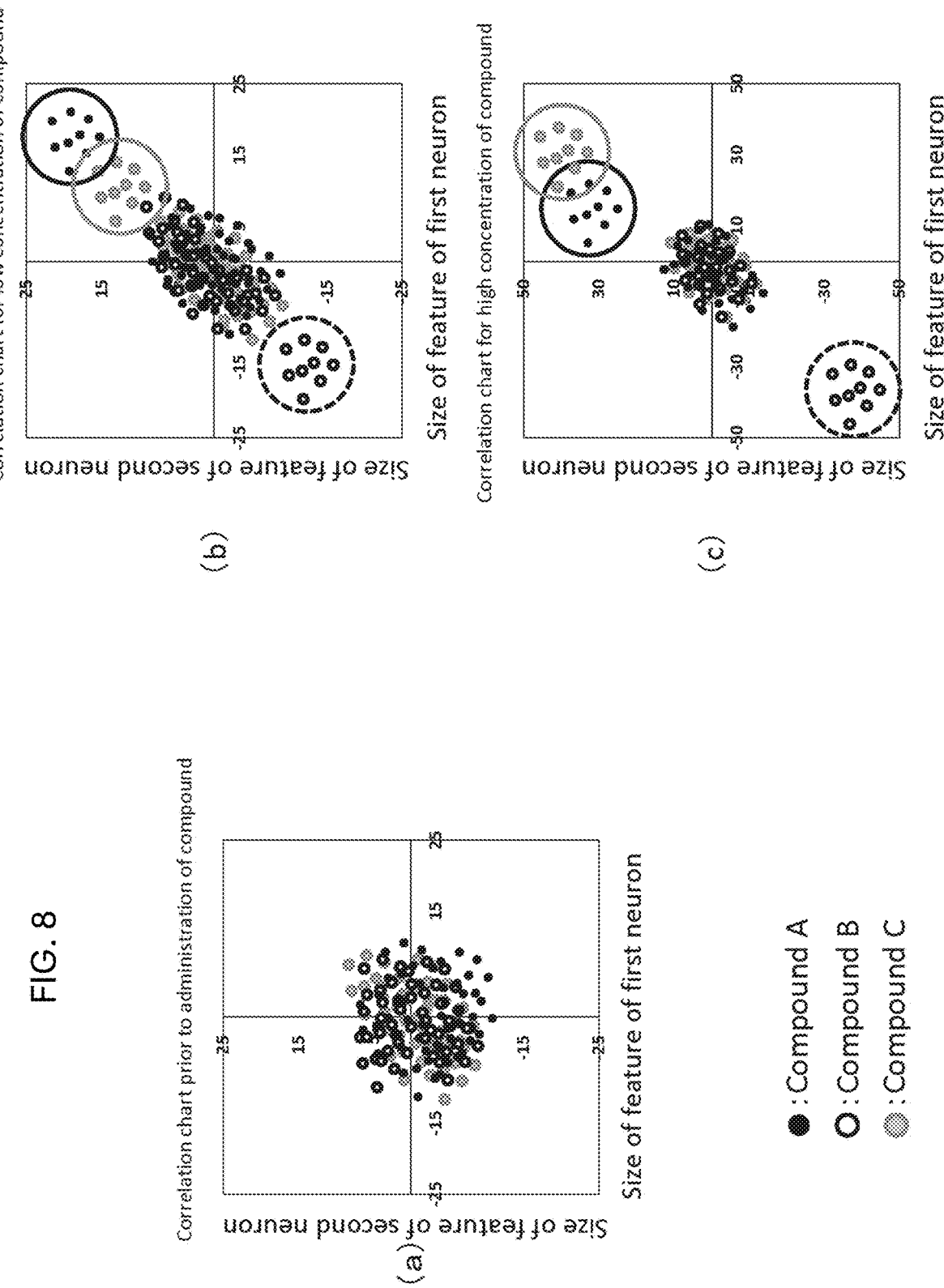
FIG. 8 is a chart showing the correlation between a feature with respect to a first neuron extracted at step S701 and a feature with respect to a second neuron extracted at step S702 for each of compounds A to C.

The comparison includes, for example, finding the correlation between the feature of the known compound with respect to the first neuron extracted at step S701 and the feature of the known compound with respect to the second neuron extracted at step S702, which includes, for example, finding the correlation of each feature as shown in FIG. 8. In this regard, a feature that changes in a concentration dependent manner among features correlating with the relationship of y=x can be determined as the feature that is characteristic to the known compound.

FIG. 8 is an example of a chart showing the correlation between a feature with respect to a first neuron extracted at step S701 and a feature with respect to a second neuron extracted at step S702 for each of compounds A to C. The horizontal axis indicates the size of the feature with respect to the first neuron, and the vertical axis indicates the size of the feature with respect to the second neuron.

FIG. 8(*a*) is a correlation chart showing the correlation between a feature extracted by the feature extraction model 1232 from an image from activity data for a first neuron prior to administration of a compound and a feature extracted by the feature extraction model 1232 from an image from activity data for a second neuron prior to administration of a compound. A significant correlation is not observed in FIG. 8(*a*) for each of compounds A to C.

FIG. 8(*b*) is a correlation chart showing the correlation between a feature extracted by the feature extraction model 1232 from an image from activity data for a first neuron after administration of a compound at a first concentration and a feature extracted by the feature extraction model 1232 from an image from activity data for a second neuron after administration of a compound at a first concentration. A correlation of y=x was generally observed in FIG. 8(*b*) for each of compounds A to C.

FIG. 8(*c*) is a correlation chart showing the correlation between a feature extracted by the feature extraction model 1232 from an image from activity data for a first neuron after administration of a compound at a second concentration and a feature extracted by the feature extraction model 1232 from an image from activity data for a second neuron after administration of a compound at a second concentration, wherein the second concentration is higher than the first concentration. A correlation of y=x was also generally observed in FIG. 8(*c*) for each of compounds A to C. Among features with a correlation of y=x, the encircled features have a greater size at a higher concentration (FIG. 8(*c*)) than the first concentration (FIG. 8(*b*)), so that the features can be considered features that change in a concentration dependent manner. Therefore, the encircled features are identified as features that are characteristic to compounds A to C, respectively.

Referring back to FIG. 6, at step S603, a feature used in learning can be normalized to use a normalized feature in learning. Normalization is performed by using, for example, a feature extracted by the feature extraction model 1232 from an image from activity data for a neuron prior to administration of a known compound. For example, normalization is performed by dividing a dimension corresponding to a feature used in learning by a feature extracted by the feature extraction model 1232 from an image from activity data for a neuron prior to administration of a known compound. If, for example, an image from activity data for a neuron prior to administration of a known compound is a divided image, normalization is performed by computing the mean value of each feature from divided images from activity data for a neuron prior to administration of a known compound for each dimension, and dividing the corresponding dimension of a feature used in learning by the mean value. Normalization can also be performed, for example, by dividing the corresponding dimension of a feature used in learning by a feature of a vehicle. Normalization makes a change in a feature prominent so that the accuracy of learning improves. Since a prominent change can be seen regardless of the number of firing of a cell, normalization also leads to a reduced difference between samples.

At Step S603, a feature that is characteristic to a known compound identified by the processing described in reference to FIG. 7 can be utilized to learn only a training data set having a feature similar to the feature that is characteristic to the known compound. This is performed, for example, by determining whether a training data set has a feature similar to the identified feature that is characteristic to the known compound, and excluding the set, when there is no similar feature, as an outlier value from a training data set for learning. The final accuracy of prediction by the image recognition model 123 is further improved by detecting an outlier value and excluding data comprising the outlier value from a training data set for learning.

The step of detecting an outlier value from a feature that is characteristic to a known compound described above can also be utilized in other applications. The step is effective in, for example, lot difference check, quality check, or selection of a cell from different cell species in the manufacture of cells or the like. For example in the manufacture of cells, an outlier value can be detected by performing the processing described in reference to FIG. 7 on at least some of the cells of a plurality of lots to identify a characteristic feature and determining whether there is a feature similar to the identified characteristic feature for cells of each of the plurality of lots. This allows exclusion of a lot with a large inter-lot difference. For example in the manufacture of cells, an outlier value can be detected by performing the processing described in reference to FIG. 7 on cells with a desirable quality to identify a characteristic feature and determining whether there is a feature similar to the identified characteristic feature for each of the plurality of cells. This allows exclusion of cells without the desired quality. For example, when selecting a cell from different cell species, an outlier value can be detected by performing the processing described in reference to FIG. 7 on cells with a desired property to identify a characteristic feature and determining whether there is a feature similar to the identified characteristic feature for cell of each of the plurality of cell species. This allows exclusion of cell species without the desired property.

The processing 500 shown in FIG. 5 did not consider the concentration of a known compound administered to a neuron, but it can be preferable to perform the processing 500 after identifying the optimal learning concentration of the known compound. This is because the final accuracy of prediction by the image recognition model 123 improves significantly.

The optimal learning concentration of a known compound can be determined, for example, by processing activity data for a neuron obtained at each of a plurality of concentrations in the same manner as step S501 and step S502 (step S601, step S602, and step S603) described above to construct a plurality of concentration unique property prediction models and comparing the prediction accuracy of each concentration unique property prediction model. Each of the plurality of concentration unique prediction models can predict and output a property of a known compound when an image (or divided image) from activity data for a neuron in response to the known compound is inputted in the same manner as the property prediction model 1233 described above. Prediction accuracy for each concentration unique property prediction model is determined based on the ratio of the correct numbers to the number of inputted images to identify a concentration unique property prediction model with the highest prediction accuracy. The concentration used by the identified concentration unique property prediction model can be identified thereby as the optimal learning concentration of the known compound.

An image recognition model 123 trained with data for the optimal learning concentration can be constructed by the processing 500 using activity data for a neuron in response to a known compound administered at the identified optimal learning concentration. The prediction accuracy is improved compared to an image recognition model 123 trained with data for anther concentration, or an image recognition model 123 trained without taking concentration into consideration.

The image recognition model 123 for predicting a property of a target compound constructed in this manner can be utilized in processing for predicting a property of the target compound described below.

Figure 9:
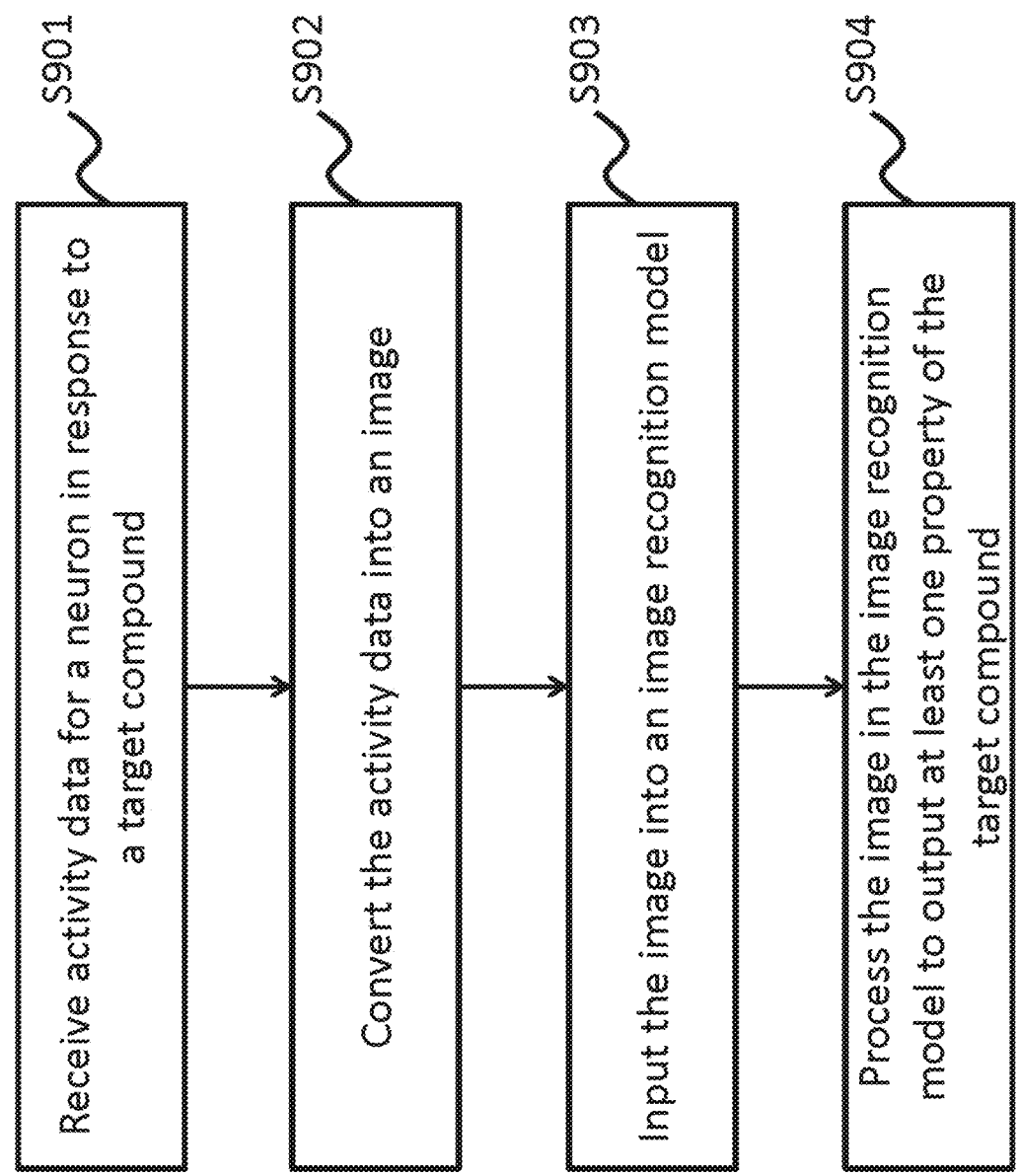
FIG. 9 is a flowchart showing an example of processing in the computer system 100 for predicting a property of a target compound.

FIG. 9 shows an example of processing in the computer system 100 for predicting a property of a target compound. The example shown in FIG. 9 describes processing 900 for predicting a property of a target compound.

At step S901, the computer system 100 receives activity data for a neuron in response to a target known compound via the receiving means 110. The received activity data is passed along to the processor 120.

At step S902, the processor 120 converts the received activity data into an image. For example, the image converting means 121 of the processor 120 converts the received activity data into at least one of a raster plot image, histogram, waveform image, spectrum intensity map from FFT, and connection map using cross-correlation as an indicator.

At step S903, the processor 120 inputs the converted image into the image recognition model 123. The image recognition model is trained by the processing 500 described above in reference to FIG. 5.

At step S904, the processor 120 processes the image in the image recognition model 123 and outputs at least one property of the target compound. In this manner, at least one property of the target compound can be predicted.

Figure 10:
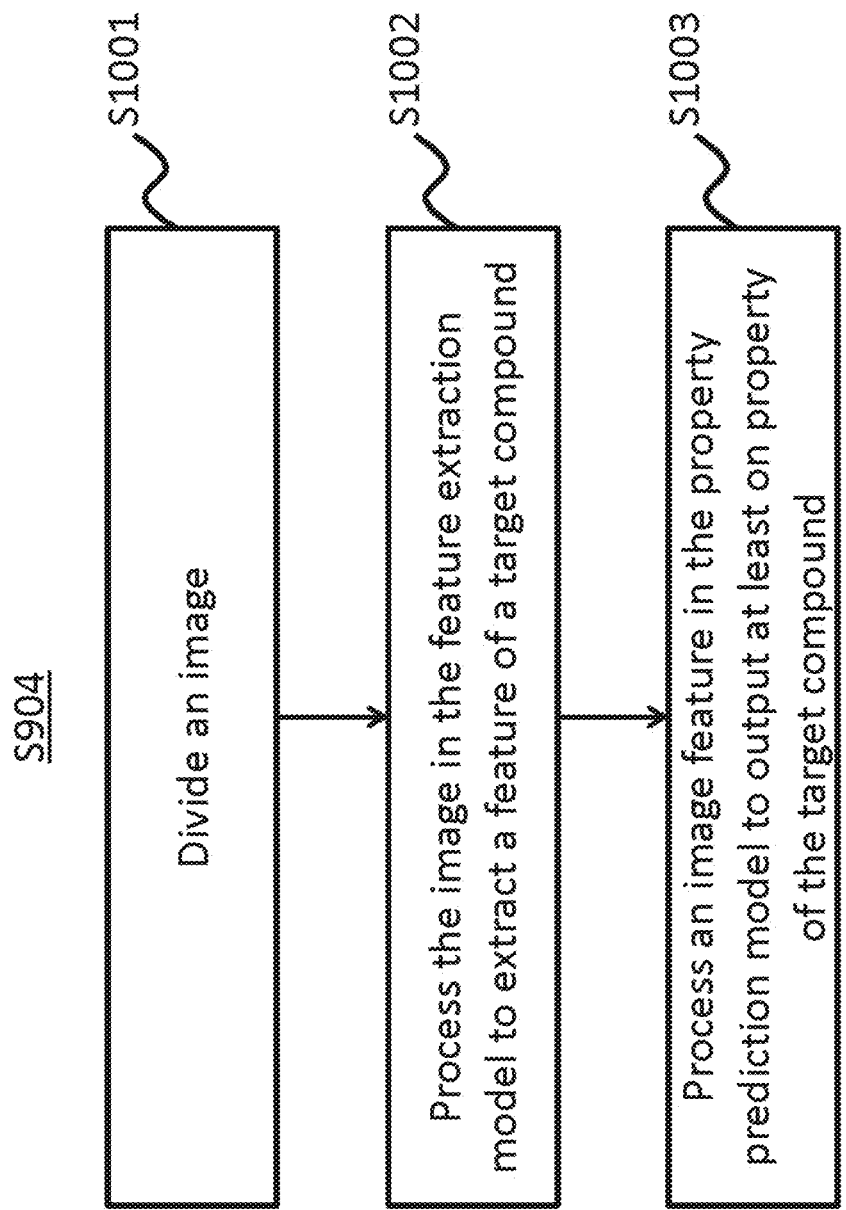
FIG. 10 is a flowchart showing an example of processing for the processor 120 to output at least one property of a target compound at step S904.

FIG. 10 shows an example of processing for the processor 120 to output at least one property of a target compound at step S904.

At step S1001, the image dividing means 122 of the processor 120 divides an image. For example, the image dividing means 122 divides an image based on a time window of a predetermined period with a fixed value or a variable value. It can be preferable to set a predetermined period for each image so that an image after division comprises a constant number of bursts. This is because this can make the number of bursts contained in images to be consistent and reduce the difference between samples that is present in activity data for a neuron. For example, a difference between samples can be present not only between samples supplied from different vendors, but also between samples supplied from the same vendor. For example, a difference can be present between samples within the same lot of samples supplied from the same vendor, and a difference can be present between lots, and a difference can be present between supply dates. A difference can also be present between facilities where a test is performed, and between people conducting a test. A reduction in these differences would improve the property prediction accuracy.

For example, division of an image based on the number of bursts can be accomplished by using the burst detection model 1231. It is assumed that the burst detection model 1231 has been already trained using training data that allows identification of a burst region. For example, when an image is inputted into the burst detection model 1231, the burst detection model 1231 identifies a burst region of the image. A predetermined period of a time window is then determined based on the identified burst region so that a constant number of bursts is contained. An image is divided by the time window whose predetermined period has been determined.

It can be preferable for an image inputted into the burst detection model 1231 to be a divided image. This is because processing load can be alleviated by restricting the amount of information in data used in processing. A divided image (raster plot image in this case) is generated by, for example, the following processing. First, a power spectrum is deduced by frequency analysis (e.g., FFT analysis or the like) on a histogram converted from activity data for a neuron in response to a target compound by the image converting means 121. The maximum peak frequency is then determined from the power spectrum, and a cycle is determined from the maximum peak frequency. A raster plot image converted from activity data for a neuron in response to a known compound is then divided based on the cycle to generate a divided raster plot image.

When an image is divided, and the divided image is inputted into the feature extraction model 1232, the feature extraction model 1232 extracts a feature of a target compound by processing the image at step S1002. It is assumed that the feature extraction model 1232 has been already trained with a training data set as described above. The feature extraction model 1232 extracts a multidimensional feature of an image. For example, an existing image recognition model that has completed learning, Alex Net, extracts a 4096 dimensional feature from an image.

Once a feature is extracted, at step S1003, the property prediction model 1233 outputs at least one property of a target compound by processing the feature. In this regard, it is assumed that the property prediction model 1233 has been already trained using training data to allow at least one property to be outputted from the feature as described above.

At step S1003, a feature inputted into the property prediction model 1233 can be restricted to a feature obtained from a specific neuron. If, for example, activity data has been obtained from a plurality of neurons, features from each of the plurality of neurons extracted at step S1002, excluding a feature from a specific neuron, can be inputted into the property prediction model 1233. This can exclude a neuron that is different in quality and reduce the difference between samples to improve the final prediction accuracy.

A neuron with a different quality that should be excluded can be determined, for example, based on correlation of each of the features of the plurality of neurons.

For example, correlation of features of each of the plurality of neurons whose activity data has been obtained and features of all other neurons is found. The mean of $R^2$ value for each of the plurality of neurons with other neurons is then computed. A neuron with a low mean $R^2$ value with other neurons is detected as an outlier value, and the neuron is determined as a neuron with a different quality that should be excluded.

An example of obtaining a feature from 3 neurons is described. If measurement of the correlation between a feature with respect to the first neuron and a feature with respect to the second neuron yields $R^2=0.7277$, measurement of the correlation between a feature with respect to the second neuron and a feature with respect to the third neuron yields $R^2=0.3071$, and measurement of the correlation between a feature with respect to the third neuron and a feature with respect to the first neuron yields $R^2=0.3954$, the means of the $R^2$ values with other neurons is 0.540 for the first neuron, 0.652 for the second neuron, and 0.351 for the third neuron. Since the $R^2$ value for the third neuron is the smallest, the third neuron can be determined as the neuron with a different quality that should be excluded. At step S1003, features excluding the feature from the third neuron are inputted into the feature prediction model 1233.

The above example described that a neuron resulting in the smallest mean $R^2$ value is excluded, but a plurality of neurons with a small mean $R^2$ value can be excluded. Alternatively, another value can be used in place of the mean $R^2$ value.

A neuron with a different quality that should be excluded can be determined, for example, based on a characteristic feature that can be identified by the same processing as the processing described above in reference to FIG. 7. For example, in the same manner as the processing described above in reference to FIG. 7, a feature that is characteristic to a target compound is identified by extracting a feature of target compound with respect to a first neuron among a plurality of neurons, extracting a feature of a target compound with respect to a second neuron among a plurality of neurons, and comparing the extracted feature of a target compound with respect to the first neuron with the extracted feature of a target compound with respect to the second neuron. A neuron with an outlier value can be excluded after detecting the outlier value by determining whether there is the same feature as the identified characteristic feature for each of the plurality of neurons.

At step S1003, the feature extracted at step S1002 can be normalized, and the normalized feature can be inputted into the property prediction model 1233. Normalization is performed, for example, using a feature extracted by the feature extraction model 1232 from an image from activity data for a neuron prior to administration of a target compound. For example, normalization is performed by dividing the feature extracted at step S1002 by a feature extracted by the feature extraction model 1232 from an image from activity data for a neuron prior to administration of a target compound. If, for example, an image from activity data for a neuron prior to administration of a known compound is a divided image, normalization is performed by computing a mean value of each feature from a divided image from activity data for a neuron prior to administration of a known compound for each dimension, and dividing the corresponding dimension of the feature extracted at step S1002 by the mean value. Normalization of a feature makes a change in a feature prominent so that the prediction accuracy improves. Since a prominent change can be seen regardless of the number of firing of a cell, normalization also leads to a reduced difference between samples.

At step S1003, a plurality of properties including a first property and a second property can be outputted, wherein it can be preferable for the second property to be associated with the first property. This is because this allows a property of a target compound to be predicted in stages and improves the final prediction accuracy.

If, for example, the first property is related to toxicity, and "with toxicity" is outputted as the first property, the second property can be related to a mechanism of action in a compound "with toxicity". This enables not only a simple prediction of presence/absence of toxicity, but also highly accurate prediction up to the difference in toxicity due to a difference in the mechanism of action. If, for example, "without toxicity" is outputted as the first property, the second property can be related to a mechanism of action in a compound "without toxicity". This enables highly accurate prediction up to the difference in the mechanism of action of a safe compound without toxicity.

Prediction of a property of a target compound in stages can be performed by a single property prediction model, but it can be preferable that such a prediction is performed by a plurality of property prediction models. A plurality of property prediction models are constructed so that each model can predict a different property. Processing load for learning can be alleviated by constructing a plurality of property prediction models, each targeting a different property for prediction. Further, prediction in stages using a plurality of property prediction models enable highly accurate prediction for a vague property to a specific property.

If, for example, a first property prediction model for predicting toxicity is constructed, a second property prediction model for predicting a mechanism of action of a compound with toxicity is constructed, and a third property prediction model for predicting a mechanism of action of a compound without toxicity is constructed, toxicity can be predicted using the first property prediction model, the mechanism of action can be predicted using the second property prediction model when predicted as 'with toxicity', and the mechanism of action can be predicted using the third property prediction model when predicted as 'without toxicity'.

In the example described above, processing was described as being performed in a specific order, but it should be noted that the order of each processing is not limited to the described order, and is performed in any theoretically feasible order.

In the examples described above in reference to FIGS. 5, 6, 7, 9, and 10, processing in each step shown in FIGS. 5, 6, 7, 9, and 10 is described to be materialized with the processor 120 and a program stored in the memory 130, but the present invention is not limited thereto. At least one of the processing of each step shown in FIGS. 5, 6, 7, 9, and 10 can be materialized with a hardware configuration such as a control circuit.

EXAMPLES

In one Example, activity data from administrating each of four seizure positive agents (4-AP, Chlorpromazine, Gabazine, and Pilocarpine) and two seizure negative agents (Acetaminophen and DMSO) to a neuron was obtained using MEA. In this regard, Axol Bioscience's Human iPSC-derived neural stem cells (ax0019) were used as the neurons, Alpha MED Scientific's MEA 24-well Plate-comfort was used as MEA, and Alpha MED Scientific's MED64-Presto (MED-A384iN) was used as the measurement device thereof. Activity data was obtained at each of a plurality of concentrations. 4-AP and Gabazine were used at concentrations of vehicle only, about 0.3 µM, about 1 µM, about 3 µM, about 10 µM, and about 30 µM, Chlorpromazine was used at concentrations of vehicle only, about 0.1 µM, about 0.3 µM, about 1 µM, about 3 µM, and about 10 µM, Pilocarpine and Acetaminophen were used at concentrations of vehicle only, about 0.3 µM, about 1 µM, about 3 µM, about 10 µM, about 30 µM, and about 100 µM, and DMSO was used at concentrations of about 0.1%, about 0.2%, about 0.3%, about 0.4%, and about 0.5%. The obtained data was inputted into the computer system of the invention, and an image recognition model was trained using a raster plot image converted from the obtained data and corresponding toxicity of the agent (seizure positive or seizure negative), wherein an image recognition model comprising a burst detection model, a feature extraction model, and a property prediction model was used. A raster plot image was divided so that the number of bursts contained in a single divided image would be 4 based on bursts detected by the burst detection model, and was inputted into the feature extraction model. An existing image recognition model that has completed learning, Alex Net, was utilized as the feature extraction model. A 4096 dimensional feature extracted by the feature extraction model, which was normalized with a feature of a vehicle, was inputted into the property prediction model. The property prediction model was comprised of 4096 units of input layers, 4 layers of hidden layers, and 2 layers of output layers and was trained to be able to predict toxicity (seizure positive or seizure negative).

An experiment was conducted to predict which of seizure positive or seizure negative would be predicted when unlearned data was inputted into the computer system of the invention after training the image recognition model. 5 runs were performed with 4-AP, and 4 runs were performed with Chlorpromazine, Gabazine, Pilocarpine, Acetaminophen, and DMSO.

Figure 11:
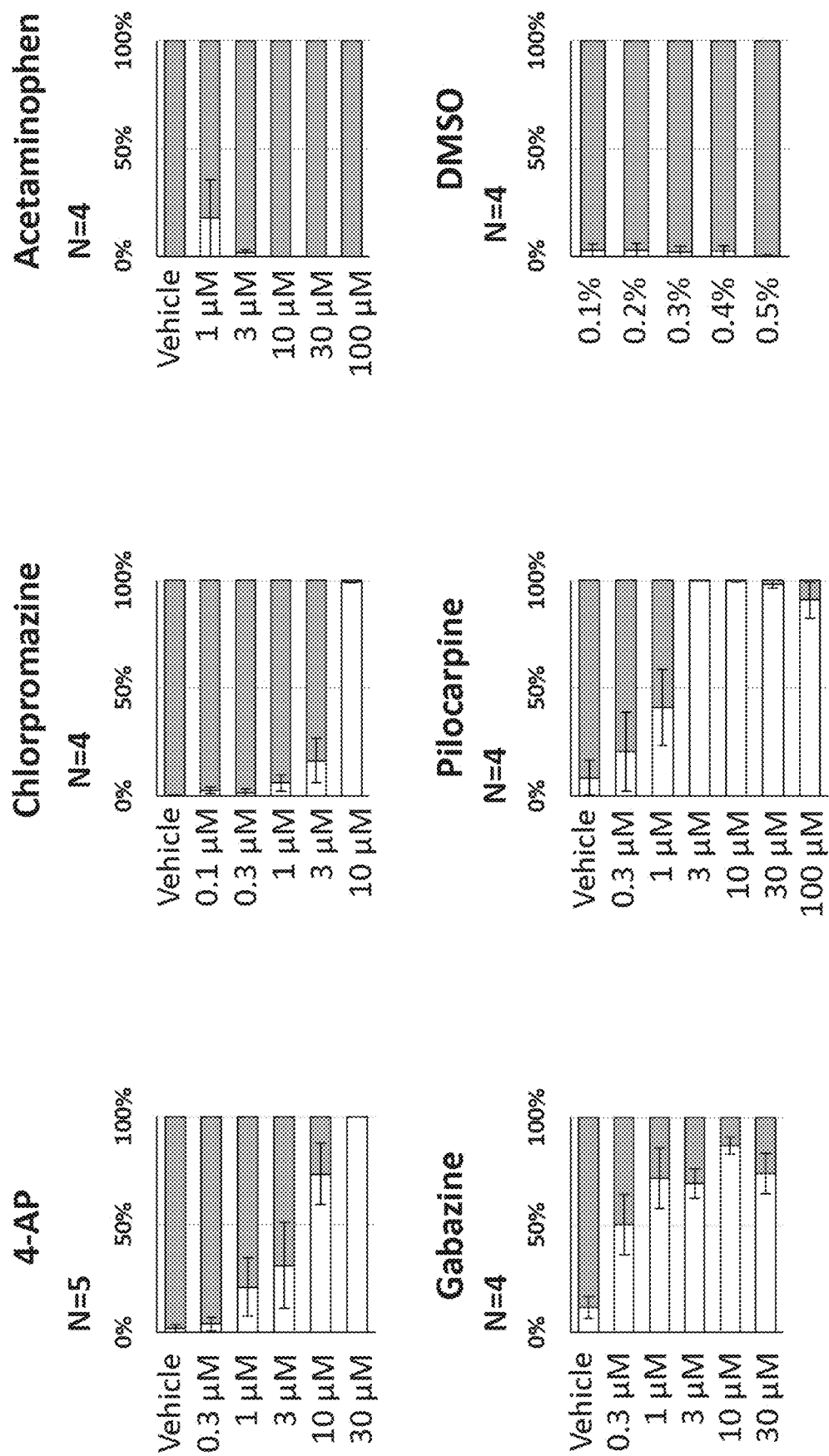
FIG. 11 is a diagram showing a result of predicting a property of an agent in one Example.

FIG. 11 is a diagram showing a result of predicting a property of an agent in this Example. Each graph shows a prediction result for a property of an agent when unlearned data for a corresponding agent is administered. White graphs indicate the mean of the ratio predicting a seizure positive property, and gray graphs indicate the mean of the ratio predicting a seizure negative property. The highest prediction accuracy for each agent was 4-AP: 100%, Chlorpromazine: 97.5%, Acetaminophen: 100%, Gabazine: 87.9%, Pilocarpine: 99.9, and DMSO: 100%, achieving on average about 98.0% prediction accuracy.

In another embodiment, activity data from administrating each of four seizure positive agents (4-AP, Chlorpromazine, Gabazine, and Pilocarpine) with different mechanisms of action to neurons was obtained using MEA. In this regard, Axol Bioscience's Human iPSC-derived neural stem cells (ax0019) were used as the neurons, Alpha MED Scientific's MEA 24-well Plate-comfort was used as MEA, and Alpha MED Scientific's MED64-Presto (MED-A384iN) was used as the measurement device thereof. 4-AP has a mechanism of action of a $K^+$ channel blocker, Chlorpromazine has a mechanism of action of a D2 dopamine receptor antagonist, Gabazine has a mechanism of action of a GABAA receptor antagonist, and Pilocarpine has a mechanism of action of a Muscarine receptor antagonist. The obtained data was inputted into the computer system of the invention, and an image recognition model was trained using a raster plot image converted from the obtained data and corresponding mechanism of action of the agent, wherein an image recognition model comprising a burst detection model, a feature extraction model, and a property prediction model was used. A raster plot image was divided so that the number of bursts contained in a single divided image would be 4 based on bursts detected by the burst detection model, and was inputted into the feature extraction model. An existing image recognition model that has completed learning, Alex Net, was utilized as the feature extraction model. A 4096 dimensional feature extracted by the feature extraction model, which was normalized with a feature of a vehicle, was inputted into the property prediction model. The property prediction model was comprised of 4096 units of input layers, 5 layers of hidden layers, and 4 layers of output layers and was trained to be able to predict the mechanism of action of an agent.

An experiment was conducted to predict which mechanism of action would be predicted when unlearned data was inputted into the computer system of the invention after training the image recognition model.

Figure 12:
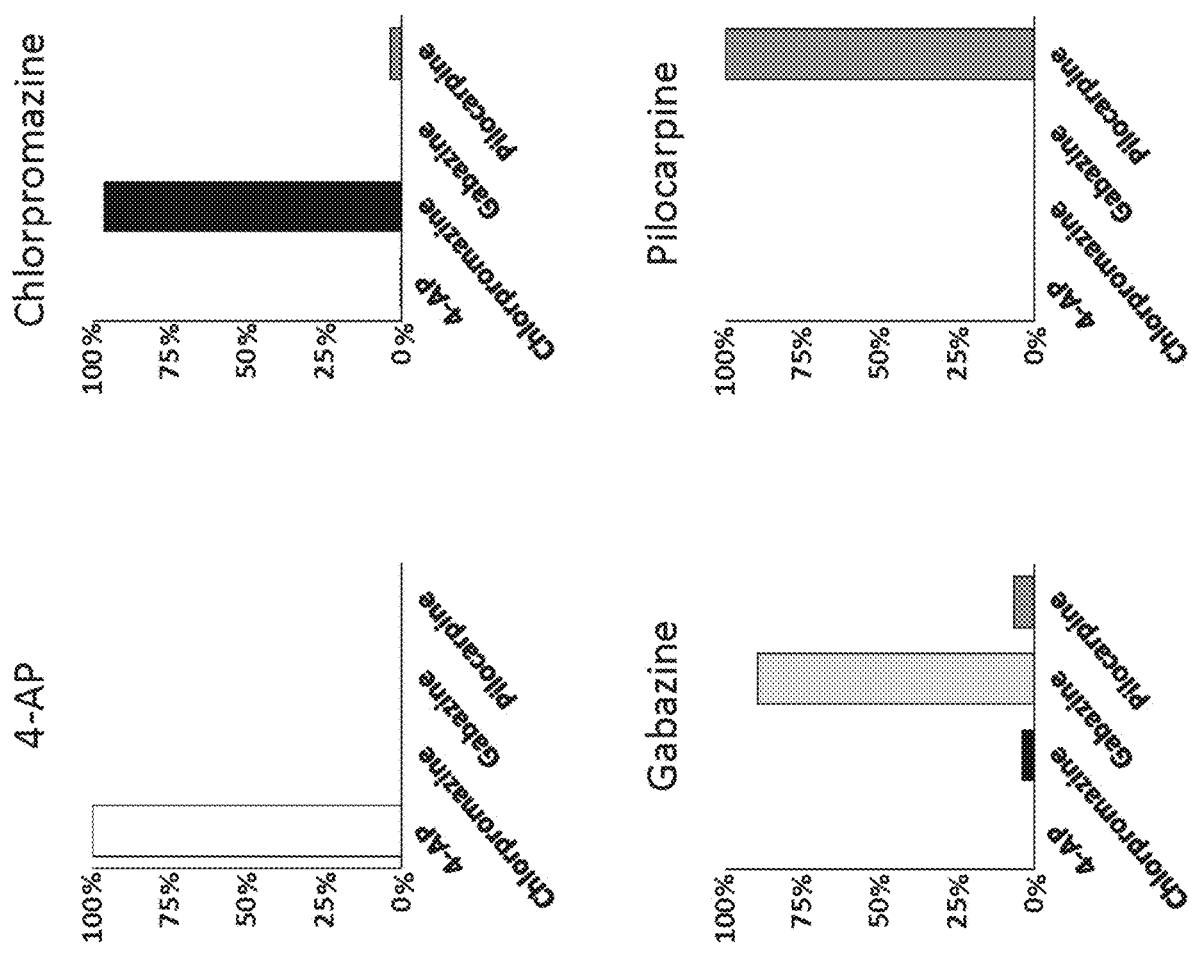
FIG. 12 is a diagram showing a result of predicting a mechanism of action in one Example.

FIG. 12 is a diagram showing a result of predicting a mechanism of action in this Example. Each graph shows a result of predicting a mechanism of action of an agent when unlearned data for a corresponding agent is administered. White graphs indicate the mean of the ratio predicting the mechanism of action of 4-AP (K+ channel blocker), black graphs indicate the mean of the ratio predicting the mechanism of action of Chlorpromazine (D2 dopamine receptor antagonist), light gray graphs indicate the mean of the ratio predicting the mechanism of action of Gabazine (GABAA receptor antagonist), and dark gray graphs indicate the mean of the ratio predicting the mechanism of action of Pilocarpine (Muscarine receptor antagonist). The mechanism of action was able to be predicted at a high accuracy for each agent (4-AP: 100%, Chlorpromazine: 96.4%, Gabazine: 97.0%, and Pilocarpine: 100%), achieving on average about 98.4% prediction accuracy.

The present invention is not limited to the aforementioned embodiments. It is understood that the scope of the present invention should be interpreted solely from the scope of the claims. It is understood that those skilled in the art can implement an equivalent scope, based on the descriptions of the invention and common general knowledge, from the descriptions of the specific preferred embodiments of the invention.

INDUSTRIAL APPLICABILITY

The present invention is useful as an invention providing a method of predicting an unknown property of a target compound in a non-clinical trial and the like.

REFERENCE SIGNS LIST

100 Computer system
110 Receiving means
120 Processor
130 Memory
140 Outputting means
200 Database unit

The invention claimed is:

1. A method of predicting at least one property of a target compound, comprising the steps of:
    (1) receiving activity data for a neuron in response to the target compound;
    (2) converting the activity data into a raster plot image, wherein the raster plot image represents times when spikes of a neuron occur;
    (3) inputting the raster plot image into an image recognition model trained with a training data set, the training data set comprising a plurality of training images from converting activity data for a neuron in response to a plurality of known compounds, the plurality of training images being raster plot images; and
    (4) processing the raster plot image in the image recognition model to output at least one property of the target compound.

2. The method of claim 1, wherein the activity data for the neuron is obtained using one of a micro-electrode array, $Ca^{2+}$ imaging, and membrane potential imaging.

3. The method of claim 1, wherein the training data set comprises a divided training image from dividing the training images by a specific time window.

4. The method of claim 3, wherein the time window is a constant time.

5. The method of claim 3, wherein the time window is set for each of the plurality of training images so that the divided training image comprises a constant number of bursts.

6. The method of claim 1, wherein the bursts are detected by converting a plurality of pieces of activity data detected using a micro-electrode array on the neuron into a plurality of raster plot images, arranging the raster plot images in accordance with the number of plots, and detecting a burst in the plurality of arranged raster plot images.

7. The method of claim 1, wherein the image recognition model comprises a property prediction model trained with a training data set and a feature extraction model trained with a training data set, wherein the step (4) comprises:
    processing the image in the feature extraction model to extract a feature of the target compound; and
    processing the extracted feature in the property prediction model to output at least one property of the target compound,
    optionally, the training data set for the property prediction model comprises features of the known compounds.

8. The method of claim 7, wherein the training data set for the property prediction model is prepared by steps of:
    identifying an optimal learning concentration of the known compounds;
    converting activity data for a neuron in response to known compounds at the optimal learning concentration into an image; and
    processing the image in the feature extraction model to extract the features of the known compounds.

9. The method of claim 7, wherein the training data set for the property prediction model is from normalizing features obtained from the activity data for the neuron in response to the known compounds with a feature obtained from the activity data for the neuron prior to administering the known compounds.

10. The method of claim 7, wherein the image recognition model further comprises a burst detection model trained with a training data set, wherein the step (4) comprises:
    processing the image in the burst detection model to detect a burst;
    dividing the image based on the detected burst and processing the divided image in the feature extraction model to extract a feature of the target compound; and
    processing the extracted feature in the property prediction model to output at least one property of the target compound.

11. The method of claim 10, wherein the image inputted into the burst detection model is prepared by steps of:
    determining a cycle by analyzing a frequency of activity data for a neuron in response to the target compound; and
    dividing the image based on the cycle.

12. The method of claim 11, wherein the analysis of a frequency of activity data comprises FFT analysis on a histogram obtained from the activity data.

13. The method of claim 7, wherein the training data set for the property prediction model is prepared by steps of:
    extracting features of the known compounds with respect to a first neuron sample by processing a plurality of images from converting activity data for the first neuron sample in response to the known compounds in the feature extraction model;
    extracting features of the known compounds with respect to a second neuron sample by processing a plurality of images from converting activity data for the second neuron sample in response to the known compounds in the feature extraction model; and
    comparing the features of the known compounds with respect to the first neuron sample with the features of the known compounds with respect to the second neuron sample to identify a feature that is characteristic to the known compounds.

14. The method of claim 7, wherein the step (4) further comprises:
    processing a plurality of images from converting activity data for a plurality of neuron samples in response to the target compound in the feature extraction model to extract a feature of the target compound with respect to each of the plurality of neuron samples; and identifying a feature inputted into the property prediction model from correlation of features of the target compound with respect to each of the plurality of neuron samples.

15. The method of claim 1, wherein the step (4) comprises:

processing the image in the image recognition model to output a plurality of properties comprising a first property and a second property of the target compound;

wherein the second property is associated with the first property.

16. The method of claim 15, wherein the image recognition model comprises a plurality of property prediction models trained with a training data set, wherein the step (4) comprises the steps of:

outputting the first property of the target compound using a first property prediction model;

determining, from the plurality of property prediction models, a second property prediction model capable of predicting the second property associated with the first property; and outputting the second property of the target compound using the second property prediction model.

17. The method of claim 1, wherein the neuron is a neural stem cell and optionally, the neural stem cell is an iPS cell.

18. The method of claim 1, wherein the at least one property comprises one or more of efficacy, toxicity, and mechanism of action of the compound.

19. A non-transitory computer-readable medium having stored therein a program for predicting at least one property of a target compound, the program, when being executed in a computer system comprising a processor, causing the processor to execute processing comprising the steps of:

(1) receiving activity data for a neuron in response to the target compound;

(2) converting the activity data into a raster plot image, wherein the raster plot image represents times when spikes of a neuron occur;

(3) inputting the raster plot image into an image recognition model trained with a training data set, the training data set comprising a plurality of training images from converting activity data for a neuron in response to a plurality of known compounds, the plurality of training images being raster plot images; and (4) processing the raster plot image in the image recognition model to output at least one property of the target compound.

20. A computer system for predicting at least one property of a target compound, the computer system comprising:

at least one computer processor, the processor configured to;

receive activity data for a neuron in response to the target compound;

convert the activity data into a raster plot image wherein the raster plot image represents times when spikes of a neuron occur;

input the raster plot image into an image recognition model trained with a training data set, the training data set comprising a plurality of training images from converting activity data for a neuron in response to a plurality of known compounds, the plurality of training images being raster plot images; and process the raster plot image in the image recognition model to output at least one property of the target compound.

* * * * *